(12) United States Patent
Voth

(10) Patent No.: US 8,909,502 B2
(45) Date of Patent: Dec. 9, 2014

(54) METHOD AND SYSTEM FOR CONSTRUCTING AN ELECTROPHYSIOLOGY MAP

(75) Inventor: Eric J. Voth, Maplewood, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 399 days.

(21) Appl. No.: 13/339,465

(22) Filed: Dec. 29, 2011

(65) Prior Publication Data

US 2013/0173222 A1    Jul. 4, 2013

(51) Int. Cl.
G06F 17/50    (2006.01)
G06F 19/00    (2011.01)

(52) U.S. Cl.
CPC ........ G06F 17/5018 (2013.01); G06F 19/3437 (2013.01)
USPC ............................................................ 703/1

(58) Field of Classification Search
CPC .. G06F 17/50; G06F 19/3437; G06F 17/5018
USPC ............................................................ 703/1
See application file for complete search history.

(56) References Cited

U.S. PATENT DOCUMENTS

| | | | |
|---|---|---|---|
| 5,966,140 A * | 10/1999 | Popovic et al. | ............... 345/441 |
| 6,233,476 B1 | 5/2001 | Strommer et al. | |
| 6,377,865 B1 | 4/2002 | Edelsbrunner et al. | |
| 6,498,944 B1 | 12/2002 | Ben-Haim et al. | |
| 6,690,963 B2 | 2/2004 | Ben-Haim et al. | |
| 6,788,967 B2 | 9/2004 | Ben-Haim et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 7,774,051 B2 | 8/2010 | Voth | |
| 7,825,925 B2 | 11/2010 | Voth | |
| 2004/0254437 A1 * | 12/2004 | Hauck et al. | .................. 600/374 |
| 2007/0073179 A1 | 3/2007 | Afonso et al. | |
| 2007/0270705 A1 | 11/2007 | Starks | |
| 2009/0167755 A1 | 7/2009 | Voth | |
| 2009/0171627 A1 | 7/2009 | Olson | |
| 2010/0274123 A1 | 10/2010 | Voth | |

OTHER PUBLICATIONS

Guo, Baining et al., "Surface Reconstruction Using Alpha Shapes," Computer Graphics forum, vol. 16, No. 4, pp. 177-190 (1997).
"International Search Report & Written Opinion", PCT/US2012/022682 May 23, 2012.

* cited by examiner

*Primary Examiner* — Dwin M Craig
(74) *Attorney, Agent, or Firm* — Dykema Gossett PLLC

(57) ABSTRACT

A method of constructing an EP map is provided. The method comprises obtaining a first surface model of an anatomic structure, the first model comprising an alpha shell of a cloud of location data points. The method further comprises obtaining a second surface model of the structure, the second surface model comprising an alpha shell of a cloud of measurement points. The method further comprises processing the first and second models to identify, for at least one of the location data points, a point on the second surface model that is closest in distance to the location data point, wherein said identified point has a value of said EP parameter associated therewith. The method still further comprises assigning a visual indicator to the location data point based on the EP parameter value associated with the identified point and in accordance with a visualization scheme corresponding to the EP parameter.

20 Claims, 16 Drawing Sheets

METHOD AND SYSTEM FOR CONSTRUCTING AN ELECTROPHYSIOLOGY MAP

BACKGROUND OF THE INVENTION a. Field of the Invention

The present invention relates generally to a method and system for constructing an electrophysiology map. More particularly, the present invention relates to a computer-implemented method and system for mapping electrophysiological information onto a multi-dimensional geometric model of an anatomic structure, such as, for example, the heart or a particular portion thereof.

b. Background Art

For many years, computer-implemented methods and systems have been used to generate or construct multi-dimensional surface models of anatomic structures, and/or to map electrophysiological (EP) information corresponding to anatomic structures onto multi-dimensional surface models thereof. More specifically, a variety of methods or techniques have been used to construct surface models of structures of the heart (i.e., cardiac structures), and/or to map EP information relating to the cardiac structures onto surface models thereof, thereby forming EP maps of the cardiac structure.

For example, in accordance with one conventional EP mapping technique, and in general terms, a multi-dimensional model of a cardiac structure is obtained comprising position information for a plurality of location data points on the surface of the cardiac structure. An EP map comprising position information for a plurality of measurement points and EP measurements made at each measurement point is also obtained. Once the model and the map are obtained, a location data point of the model is chosen, and the two measurement points of the EP map that are closest to the chosen location data point are determined. The Delaunay triangulation technique is then used to define a Delaunay edge between the two measurement points determined to be the closest measurement points to the chosen location data point. The aforedescribed process is then repeated for each of the location data points in the model, resulting in the definition of a plurality of Delaunay edges.

Once the process is complete for each location data point, the Delaunay edges are connected to form a plurality of triangles. One of the location data points from the model is then selected, and the triangle formed of Delaunay edges that surrounds the selected location data point is identified. A value or level of the EP parameter being mapped is then assigned to the location data point based on interpolation using the EP measurements measured at each of the vertices (i.e., measurement points) of the identified triangle. This process is then repeated for each of the location data points until each location data point has a value of the EP parameter assigned thereto.

Once a location data point has an EP parameter value or level assigned thereto, a color or some other visual indicator is assigned to the location data point based on the relative magnitude of the EP parameter value assigned to the location data point. The model is then presented using the color(s) or other visual indicator(s) assigned to the location data point(s).

Techniques such as that described above, however, are not without their disadvantages. For example, in the above described technique, because each location data point of the model is evaluated and a Delaunay edge defined for each, then a plurality of triangles are formed from the plurality of edges, and then an EP value assigned to the location data point based on an interpolation of EP measurements of three measurement points, all before a visual indicator is assigned, the mapping process is very time intensive. Further, the mapping process is unduly complex and, as a result, may utilize an undesirable amount of computing resources.

Accordingly, there is a need for a method and system for constructing or generating an electrophysiology map corresponding to an anatomic structure that will minimize and/or eliminate one or more of the above-identified deficiencies.

BRIEF SUMMARY OF THE INVENTION

The present invention is directed to a method and system for generating or constructing an electrophysiological (EP) map corresponding to an anatomic structure, such as, for example, a cardiac structure.

In accordance with one aspect of the invention and the present teachings, a computer-implemented method of constructing an EP map corresponding to an anatomic structure comprises obtaining a first surface model of at least a portion of the anatomic structure. In an exemplary embodiment, the first surface model comprises an alpha shell of a point cloud comprised of a plurality of location data points corresponding to respective locations on the surface of the anatomic structure. In an exemplary embodiment, the step of obtaining the first surface model comprises constructing the first surface model. In such an embodiment, the constructing step comprises acquiring the plurality of location data points forming the point cloud and computing the alpha shell of the point cloud. In an exemplary embodiment, the constructing step further comprises processing the alpha shell to generate a simplicial surface model.

The method further comprises obtaining a second surface model of at least a portion of the anatomic structure. In an exemplary embodiment, the second surface model comprises an alpha shell of a point cloud comprised of a plurality of measurement points corresponding to respective locations on the surface of the anatomic structure at which measurements of an EP parameter were made. In an exemplary embodiment, the step of obtaining the second surface model comprises constructing the second surface model. In such an embodiment, the constructing step comprises acquiring the plurality of measurement points forming the point cloud and computing the alpha shell of the point cloud. In an exemplary embodiment, the constructing step further comprises processing the alpha shell to generate a simplicial surface model. Further, in an exemplary embodiment, the steps of obtaining the first and second surface models are performed simultaneously.

The method still further comprises processing the first and second surface models to identify, for at least one of the location data points of the first surface model, a point on the second surface model that is closest in distance to the location data point, wherein the identified point has a value of the EP parameter associated therewith.

In an exemplary embodiment, the method further comprises the step of associating the EP parameter value with the identified point on the second surface model. The associating step may comprise interpolating the EP parameter value from a plurality of EP parameter measurements, or may comprise correlating a value corresponding to an EP parameter measurement made at one of the measurement points with the identified point.

The method yet still further comprises assigning a visual indicator to the location data point based on the EP parameter value associated with the identified point on the second surface model and in accordance with a visualization scheme corresponding to the EP parameter. In an exemplary embodiment, the visualization scheme is a color coding scheme, and step of assigning a visual indicator to the location data point comprises assigning a visual indicator in the form of a color to the location data point.

In an exemplary embodiment, the method further comprises calculating the distance between the location data point and the identified point on the second surface model. In such an embodiment, the step of assigning a visual indicator to the location data point comprises assigning a visual indicator if the calculated distance is within a predetermined threshold distance.

In an exemplary embodiment, the method yet still further comprises displaying the first surface model with the visual indicator disposed thereon.

In accordance with another aspect of the invention and the present teachings, a system for constructing an EP map comprises a processing apparatus configured to obtain a first surface model of at least a portion of the anatomic structure. In an exemplary embodiment, the first surface model comprises an alpha shell of a point cloud comprised of a plurality of location data points corresponding to respective locations on the surface of the anatomic structure. In an exemplary embodiment, the processing apparatus is configured to obtain the first surface model by acquiring the plurality of location data points forming the point cloud and computing the alpha shell of the point cloud.

The processing apparatus is further configured to obtain a second surface model of at least a portion of the anatomic structure. In an exemplary embodiment, the second surface model comprises an alpha shell of a point cloud comprised of a plurality of measurement points corresponding to respective locations on the surface of the anatomic structure at which measurements of an EP parameter were made. In an exemplary embodiment, the processing apparatus is configured to obtain the second surface model by acquiring the plurality of measurement points forming the point cloud and computing the alpha shell of the point cloud.

The processing apparatus is still further configured to identify, for at least one of the location data points of the first surface model, a point on the second surface model that is closest in distance to the location data point, wherein the identified point has a value of the EP parameter associated therewith.

In an exemplary embodiment, the processing apparatus is configured to associate the EP parameter value with the identified point on the second surface model. The processing apparatus is configured to do so by interpolating the EP parameter value from a plurality of EP parameter measurements, or correlating a value corresponding to an EP parameter measurement made at one of the measurement points with the identified point.

The processing apparatus is yet still further configured to assign a visual indicator to the location data point based on the EP parameter value associated with the identified point on the second surface model and in accordance with a visualization scheme corresponding to the EP parameter.

In an exemplary embodiment, the system further comprises a display device. In such an embodiment, the processing apparatus is configured to control the display device to display the first surface model with the visual indicator disposed thereon.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
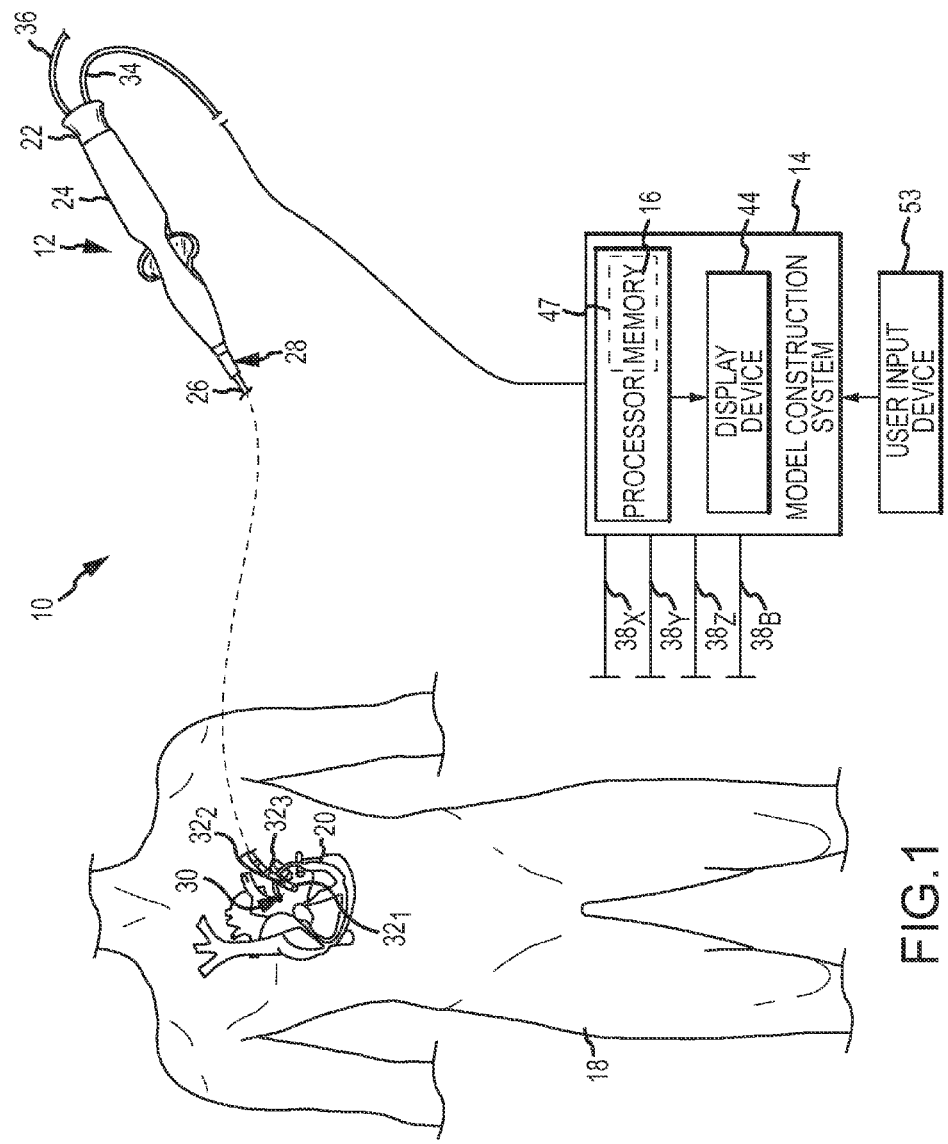
FIG. 1 is a diagrammatic view of an exemplary system for generating surface models and/or mapping electrophysiological information thereon in accordance with the present teachings.

Referring now to the drawings wherein like reference numerals are used to identify identical components in the various views, FIG. 1 illustrates one exemplary embodiment of a system 10 for mapping electrophysiological information corresponding to an anatomic structure onto a multi-dimensional (e.g., three-dimensional) geometry surface model of the anatomic structure (each of the terms "electrophysiology" and "electrophysiological" will hereinafter be referred to as "EP"). It should be noted that while the following description focuses primarily on the use of the system 10 in the construction of EP maps for cardiac structures, the present disclosure is not meant to be so limited. Rather, the system 10, and the methods and techniques used thereby, may be applied to the construction of EP maps, and/or the construction of geometry surface models, for any number of anatomic structures, including anatomic structures other than cardiac structures.

With continued reference to FIG. 1, in an exemplary embodiment, the system 10 comprises, among other components, a medical device 12 and a model construction system 14. In an exemplary embodiment, the medical device 12 comprises a catheter (catheter 12), and the model construction system 14 comprises, in part, a processing apparatus 16. The processing apparatus 16 may take the form of an electronic control unit, for example, that is configured to obtain a geometry surface model of the cardiac structure (Step 100 in FIGS. 5 and 12A), and to construct an EP map corresponding to the cardiac structure using data collected by, for example, the catheter 12 (Step 200 in FIG. 12A). As will be described in greater detail below, in an exemplary embodiment, the model construction system 14 is configured to obtain the geometry surface model by constructing or generating it using data collected by, for example, the catheter 12. In another exemplary embodiment, the model construction system 14 does not construct or generate the geometry surface model, but rather it obtains the model from a memory associated with or accessible by the model construction system 14, or from another component that is part of the system 10 or that is electrically connected to and configured for communication with the model construction system 14.

As illustrated in FIG. 1, the catheter 12 is configured to be inserted into a patient's body 18, and more particularly, into the patient's heart 20. The catheter 12 may include a cable connector or interface 22, a handle 24, a shaft 26 having a proximal end 28 and a distal end 30 (as used herein, "proximal" refers to a direction toward the portion of the catheter 12 near the clinician, and "distal" refers to a direction away from the clinician and (generally) inside the body of a patient), and one or more sensors 32 (e.g., $32_1$, $32_2$, $32_3$) mounted in or on the shaft 26 of the catheter 12. In an exemplary embodiment, the sensors 32 are disposed at or near the distal end 30 of the shaft 26. The catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

The connector 22 provides mechanical, fluid, and electrical connection(s) for cables, such as, for example, cables 34, 36 extending to the model construction system 14 and/or other components of the system 10 (e.g., a visualization, navigation, and/or mapping system (if separate and distinct from the model construction system 14), an ablation generator, irrigation source, etc.). The connector 22 is conventional in the art and is disposed at the proximal end of the catheter 12, and the handle 24 thereof, in particular.

The handle 24, which is disposed at the proximal end 28 of the shaft 26, provides a location for the clinician to hold the catheter 12 and may further provide means for steering or guiding the shaft 26 within the body 18 of a patient. For example, the handle 24 may include means to change the length of a steering wire extending through the catheter 12 to the distal end 30 of the shaft 26 to steer the shaft 26. The handle 24 is also conventional in the art and it will be understood that the construction of the handle 24 may vary. In another exemplary embodiment, the catheter 12 may be robotically driven or controlled. Accordingly, rather than a clinician manipulating a handle to steer or guide the catheter 12, and the shaft 26 thereof, in particular, in such an embodiment a robot is used to manipulate the catheter 12.

The shaft 26 is an elongate, tubular, flexible member configured for movement within the body 18. The shaft 26 supports, for example and without limitation, sensors and/or electrodes mounted thereon, such as, for example, the sensors 32, associated conductors, and possibly additional electronics used for signal processing and conditioning. The shaft 26 may also permit transport, delivery, and/or removal of fluids (including irrigation fluids, cryogenic ablation fluids, and bodily fluids), medicines, and/or surgical tools or instruments. The shaft 26 may be made from conventional materials such as polyurethane, and defines one or more lumens configured to house and/or transport electrical conductors, fluids, or surgical tools. The shaft 26 may be introduced into a blood vessel or other structure within the body 18 through a conventional introducer. The shaft 26 may then be steered or guided through the body 18 to a desired location, such as the heart 20, using means well known in the art.

The sensors 32 mounted in or on the shaft 26 of the catheter 12 are electrically connected to the model construction system 14, and the processing apparatus 16 thereof, in particular. The sensors 32 may be provided for a variety of diagnostic and therapeutic purposes including, for example and without limitation, EP studies, pacing, cardiac mapping, and ablation. In an exemplary embodiment, one or more of the sensors 32 are provided to perform a location or position sensing function. More particularly, and as will be described in greater detail below, one or more of the sensors 32 are configured to be a positioning sensor(s) that provides information relating to the location (position and orientation) of the catheter 12, and the distal end 30 of the shaft 26 thereof, in particular, at certain points in time. Accordingly, in such an embodiment, as the catheter 12 is moved along a surface of the cardiac structure and/or about the interior thereof, the sensor(s) 32 can be used to collect location data points that correspond to the surface of, or locations within, the cardiac structure. These location data points can then be used by, for example, the model construction system 14 in the construction of a geometry surface model of the cardiac structure, which will be described in greater detail below.

As will also be described in greater detail below, in addition to performing the position sensing function described above, or in the alternative, one or more of the sensors 32 may be configured to measure one or more EP parameters corresponding to the cardiac structure using techniques that are well known in the art. More particularly, as a sensor 32 that is configured to make such measurements is moved along the surface of the cardiac structure, the sensor 32 is configured to make measurements of an EP parameter of interest and to communicate the measured value(s) of the parameter to the model construction system 14. The measured value(s) of the EP parameter can then be used by, for example, the model construction system 14, in the construction of an EP map of the cardiac structure on a geometry surface model of the cardiac structure.

While in an exemplary embodiment the position sensing function and EP parameter measurement functions may be performed by different sensors, for purposes of clarity and illustration, the description below will be limited to an embodiment wherein each of the sensors 32 of the catheter 12 is configured to perform the position sensing and measurement functions. It will be appreciated, however, that embodiments wherein different sensors are used to perform the different functions remain within the spirit and scope of the present disclosure.

As will be described in greater detail below, in an exemplary embodiment, the model construction system 14, and the processing apparatus 16 thereof, in particular, is configured to obtain a geometry surface model of the cardiac surface (or at least a portion thereof), and to map EP information corresponding to that cardiac structure onto the geometry surface model. It will be appreciated that while in an exemplary embodiment the processing apparatus 16 is configured to perform all of the functionality described above and below, the present disclosure is not meant to be so limited. Rather, in other exemplary embodiments, the processing apparatus 16 is configured to perform some, but not all, of the functionality. In such an embodiment, another component or components that is/are part of the system 10 or the model construction system 14 thereof, or that is/are configured for communication with the system 10, and the processing apparatus 16 thereof, in particular, is/are configured to perform some of the functionality. Such embodiments remain within the spirit and scope of the present disclosure.

Further, in an exemplary embodiment, the processing apparatus 16 is configured to use, at least in part, data (location data and/or EP data/information) collected by the catheter 12 in the construction of one or both of a geometry surface model and an EP map. It will be appreciated that in other exemplary embodiments the location data and the EP information may be collected by different catheters or other medical devices. However, for purposes of illustration and clarity, the description below will be limited to an embodiment wherein both the location data and the EP information used to construct the geometry surface model and the EP map are collected by the catheter 12.

Accordingly, the respective processes or techniques performed by the model construction system 14 in obtaining a geometry surface model of the cardiac structure and constructing an EP map will now be described in turn below.

As briefly described above, the model construction system 14 is configured to obtain a geometry surface model of the cardiac structure (or at least a portion thereof) in one of number of ways. In one exemplary embodiment, the geometry surface model is obtained from a memory or storage device that is associated with or accessible by the model construction system 14, and the processing apparatus 16 thereof, in particular, or from another component that is part of the system 10 or that is electrically connected to and configured for communication with the model construction system 14. In another exemplary embodiment, the model construction system 14 may obtain the geometry surface model by constructing or generating it from data collected by, for example, a medical device such as the catheter 12.

In an embodiment wherein the model construction system 14 is configured to construct the geometry surface model, the model construction system 14 is configured to acquire location data points collected by the sensor(s) 32 corresponding to the cardiac structure. The model construction system 14 is configured to then use those location data points in the construction of the geometry surface model of the cardiac structure. In an exemplary embodiment, the model construction system 14 acquires the location data points by functioning with the sensors 32 to collect location data points. In another exemplary embodiment, however, the model construction system 14 may simply acquire the location data points from the sensors 32 or another component in the system 10, such as, for example, a memory or other storage device that is part of the model construction system 14 or accessible thereby, without affirmatively taking part in the collection of the location data points. In either embodiment, the model construction system 14 is configured to construct a geometry surface model based on some or all of the collected location data points. For purposes of illustration and clarity, the description below will be limited to an embodiment wherein the model construction system 14 is configured to both construct the geometry surface model and also acquire location data points by functioning with the sensor(s) 32 in the collection of the location data points. It will be appreciated, however, that embodiments wherein the model construction system 14 only acquires location data points from the sensor(s) 32 or another component of the system 10 and then constructs the geometry surface model based thereon remain within the spirit and scope of the present disclosure.

Accordingly, in an exemplary embodiment, in addition to constructing a geometry surface model of a structure, the model construction system 14 is configured to function with the sensor(s) 32 to collect location data points that are used in the construction of the geometry surface model. In such an embodiment, the model construction system 14 may comprise an electric field-based system, such as, for example, the EnSite NavX™ system commercially available from St. Jude Medical, Inc., and generally shown with reference to U.S. Pat. No. 7,263,397 entitled "Method and Apparatus for Catheter Navigation and Location and Mapping in the Heart", the entire disclosure of which is incorporated herein by reference. In other exemplary embodiments, however, the model construction system 14 may comprise other types of systems, such as, for example and without limitation: a magnetic-field based system such as the Carto™ System available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd., and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference; a combination electric field-based and magnetic field-based system such as the Carto 3™ System also available from Biosense Webster.

As briefly described above, in an exemplary embodiment, the sensor(s) 32 of the catheter 12 comprise positioning sensors. The sensor(s) 32 produce signals indicative of catheter location (position and/or orientation) information. In an embodiment wherein the model construction system 14 is an electric field-based system, the sensor(s) 32 may comprise one or more electrodes. In such an embodiment, each of the electrodes may comprise one of a number of types of electrodes, such as, for example, tip electrodes, ring electrodes, button electrodes, coil electrodes, brush electrodes, flexible polymer electrodes, and spot electrodes. Alternatively, in an embodiment wherein the model construction system 14 is a magnetic field-based system, the sensor(s) 32 may comprise one or more magnetic sensors configured to detect one or more characteristics of a low-strength magnetic field. For instance, in one exemplary embodiment, the sensor(s) 32 may comprise magnetic coils disposed on or in the shaft 26 of the catheter 12.

For purposes of clarity and illustration, the model construction system 14 will hereinafter be described as comprising an electric field-based system, such as, for example, the EnSite NavX™ system identified above. It will be appreciated that while the description below is primarily limited to an embodiment wherein the sensor(s) 32 comprise one or more electrodes, in other exemplary embodiments, the sensor(s) 32 may comprise one or more magnetic field sensors (e.g., coils). Accordingly, model construction systems that include positioning sensor(s) other than the sensors or electrodes described below remain within the spirit and scope of the present disclosure.

Figure 2:
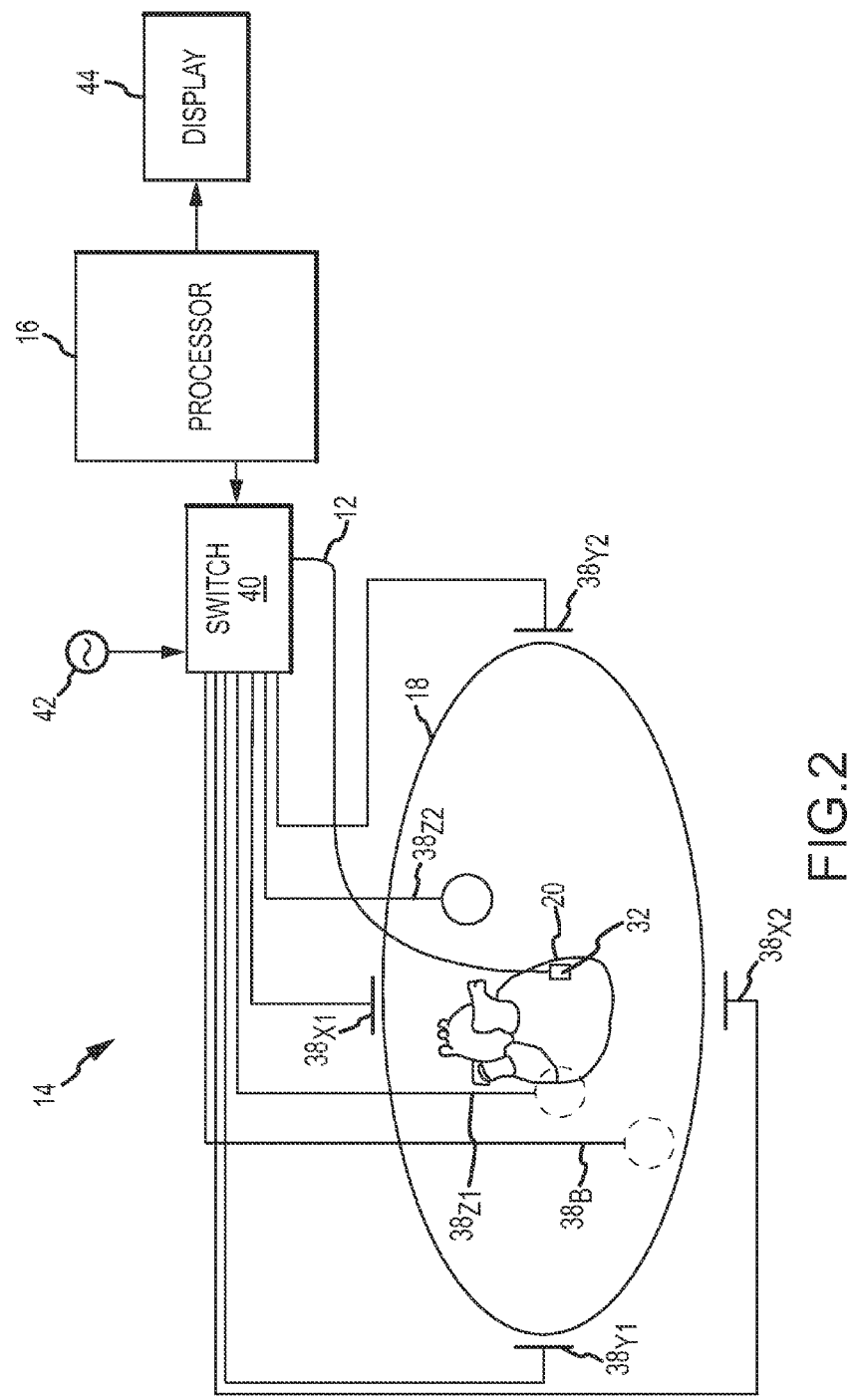
FIG. 2 is a simplified diagrammatic and schematic view of an exemplary model construction system of the system illustrated in FIG. 1.

With reference to FIG. 2, in addition to the processing apparatus 16, the model construction system 14 may include, among other possible components, a plurality of patch electrodes 38, a multiplex switch 40, a signal generator 42, and a display device 44. In another exemplary embodiment, some or all of these components are separate and distinct from the model construction system 14 but that are electrically connected to, and configured for communication with, the model construction system 14.

The processing apparatus 16 may comprise a programmable microprocessor or microcontroller, or may comprise an application specific integrated circuit (ASIC). The processing apparatus 16 may include a central processing unit (CPU) and an input/output (I/O) interface through which the processing apparatus 16 may receive a plurality of input signals including, for example, signals generated by patch electrodes 38 and the sensor(s) 32, and generate a plurality of output signals including, for example, those used to control and/or provide data to, for example, the display device 44 and the switch 40. The processing apparatus 16 may be configured to perform various functions, such as those described in greater detail above and below, with appropriate programming instructions or code (i.e., software). Accordingly, the processing apparatus 16 is programmed with one or more computer programs encoded on a computer storage medium for performing the functionality described herein.

With the exception of the patch electrode $38_B$ called a "belly patch," the patch electrodes 38 are provided to generate electrical signals used, for example, in determining the position and orientation of the catheter 12. In one embodiment, the patch electrodes 38 are placed orthogonally on the surface of the body 18 and are used to create axes-specific electric fields within the body 18. For instance, in one exemplary embodiment, patch electrodes $38_{X1}$, $38_{X2}$ may be placed along a first (x) axis. Patch electrodes $38_{Y1}$, $38_{Y2}$ may be placed along a second (y) axis, and patch electrodes $38_{Z1}$, $38_{Z2}$ may be placed along a third (z) axis. In other embodiments, the dipoles created may not be on an axis, for example a dipole between electrodes $38_{X1}$ and $38_{Y1}$. Each of the patch electrodes 38 may be coupled to the multiplex switch 40. In an exemplary embodiment, the processing apparatus 16 is configured, through appropriate software, to provide control signals to the switch 40 to thereby sequentially couple pairs of electrodes 38 to the signal generator 42. Excitation of each pair of electrodes 38 generates an electric field within body 18 and within an area of interest such as the heart 20. Voltage levels at non-excited electrodes 38, which are referenced to the belly patch $38_B$, are filtered and converted and provided to processing apparatus 16 for use as reference values.

In an exemplary embodiment, the sensor(s) 32 of the catheter 12 are electrically coupled to the processing apparatus 16 and, as described above, are configured to serve a position sensing function. More particularly, the sensor(s) 32 are placed within electric fields created in the body 18 (e.g., within the heart) by exciting the patch electrodes 38. For purposes of clarity and illustration only, the description below will be limited to an embodiment wherein a single sensor 32 is placed within the electric fields. It will be appreciated, however, that in other exemplary embodiments that remain within the spirit and scope of the present disclosure, a plurality of sensors 32 can be placed within the electric fields and then positions and orientations of each sensor can be determined using the techniques described below.

Figure 3:
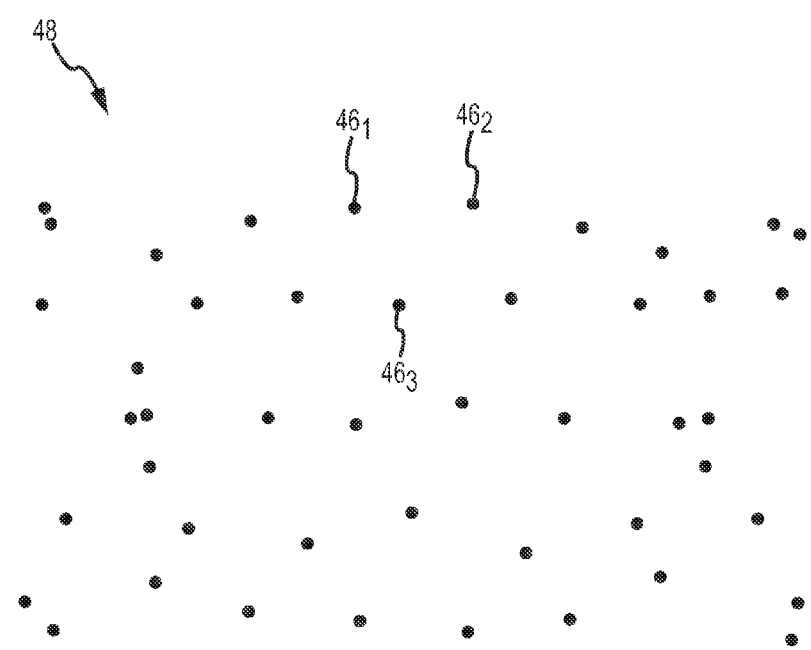
FIG. 3 is a schematic diagram of a point cloud comprised of a collection of location data points corresponding to respective locations on the surface of an anatomic structure.
Figures 4A, 4B:
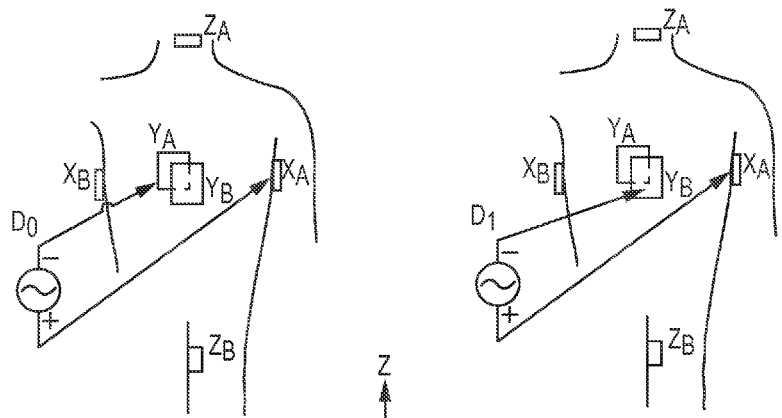
FIGS. 4A-4D are schematic diagrams of exemplary dipole pairs of driven patch electrodes suitable for use in the model construction system illustrated in FIG. 2.
Figures 4C, 4D:
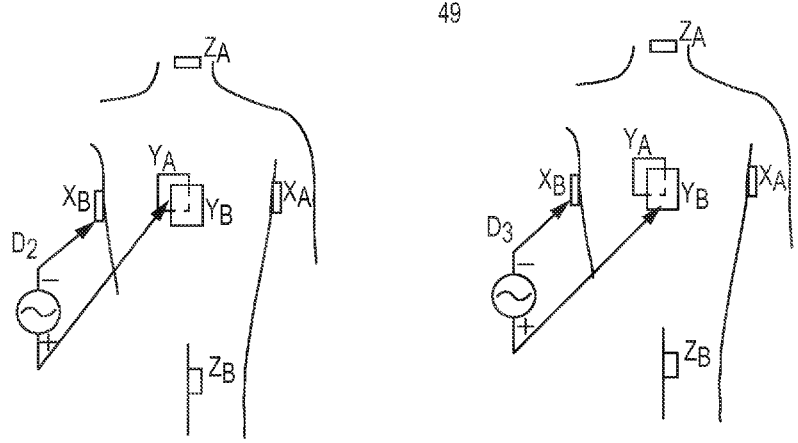

When disposed within the electric fields, the sensor 32 experiences voltages that are dependent on the location between the patch electrodes 38 and the position of the sensor 32 relative to tissue. Voltage measurement comparisons made between the sensor 32 and the patch electrodes 38 can be used to determine the location of the sensor 32 relative to the tissue. Accordingly, as the catheter 12 is swept about or along a particular area or surface of interest, the processing apparatus 16 receives signals (location information) from the sensor 32 reflecting changes in voltage levels on the sensor 32 and from the non-energized patch electrodes 38. Using various known algorithms, the processing apparatus 16 may then determine the location (position and orientation) of the sensor 32 and record it as a location data point 46 (also referred to herein as "data point 46" and illustrated in FIG. 3) corresponding to a location of the sensor 32 on the surface of, or within, the cardiac structure in a memory or storage device associated with, or accessible, by the processing apparatus 16, such as the memory 47. In an exemplary embodiment, prior to recording the location as a location data point, the raw location data represented by the signals received by the processing apparatus 16 may be corrected by the processing apparatus 16 to account for respiration, cardiac activity, and other artifacts using known or hereafter developed techniques. In any event, the collection of location data points 46 ($46_1$, $46_2$, ..., $46_n$) taken over time results in the formation of a point cloud 48 (best shown in FIG. 3) stored in the memory or storage device.

While the description above has thus far been generally with respect to an orthogonal arrangement of the patch electrodes 38, the present disclosure is not meant to be so limited. Rather, in other exemplary embodiments, non-orthogonal arrangements may be used to determine the location coordinates of the sensor 32. For example, and in general terms, FIGS. 4A-4D depict a plurality of exemplary non-orthogonal dipoles $D_0$, $D_1$, $D_2$, and $D_3$, set in a coordinate system 49. In FIGS. 4A-4D, the X-axis patch electrodes are designated $X_A$ and $X_B$, the Y-axis patch electrodes are designated $Y_A$ and $Y_B$, and the Z-axis patch electrodes are designated $Z_A$ and $Z_B$. For any desired axis, the potentials measured across an intracardiac sensor, such as sensor 32, resulting from a predetermined set of drive (source sink) configurations may be combined algebraically to yield the same effective potential as would be obtained simply by driving a uniform current along the orthogonal axes. Any two of the patch electrodes $38_{X1}$, $38_{X2}$, $38_{Y1}$, $38_{Y2}$, $38_{Z1}$, and $38_{Z2}$ (See FIG. 2) may be selected as a dipole source and drain with respect to a ground reference, e.g., the belly patch $38_B$, while the unexcited patch electrodes measure voltage with respect to the ground reference. The sensor 32 placed in the heart 20 is also exposed to the field for a current pulse and is measured with respect to ground, e.g., the belly patch $38_B$.

Data sets from each of the patch electrodes and the sensor 32 are all used to determine the location of the sensor 32 within the heart 20. After the voltage measurements are made, a different pair of patch electrodes is excited by the current source and the voltage measurement process of the remaining patch electrodes and internal sensor takes place. Once the location of the sensor 32 is determined, and as was described above, the location may be recorded as a data point 46 in the same manner described above. In an exemplary embodiment, prior to recording the location as a location data point, the raw location data represented by the signals received by the processing apparatus 16 may be corrected by the processing apparatus 16 to account for respiration, cardiac activity, and other artifacts using known or hereafter developed techniques. Accordingly, it will be appreciated that any number of techniques may be used to determine locations of the sensor 32 and to, therefore, collect data points corresponding thereto, each of which remains within the spirit and scope of the present disclosure.

Figure 5:
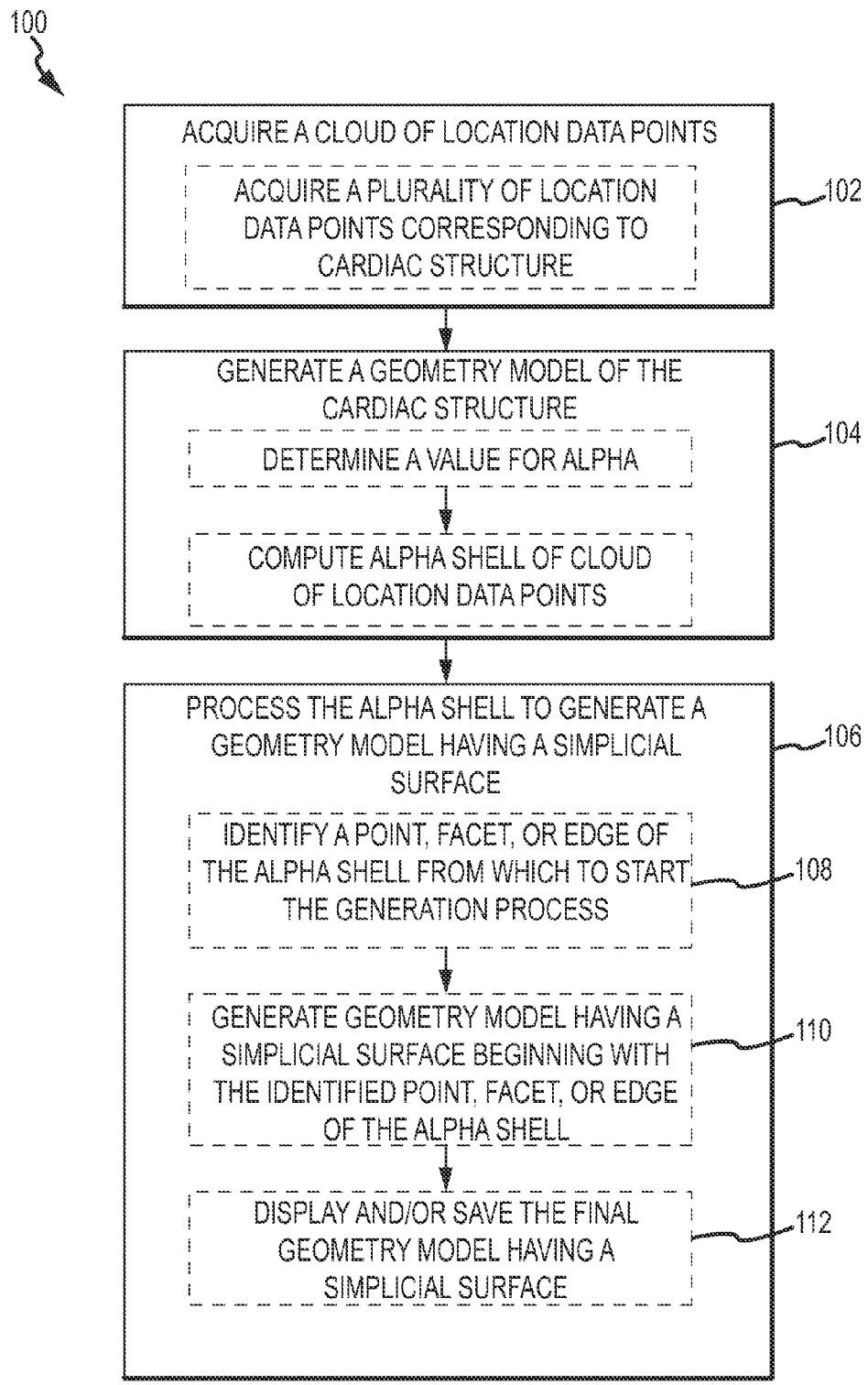
FIG. 5 is a flow chart illustrating an exemplary method of generating or a constructing a multi-dimensional geometry surface model in accordance with the present teachings.

Accordingly, and with reference to FIG. 5, in an exemplary embodiment, the processing apparatus 16 is configured to construct a geometry surface model of the cardiac structure by first acquiring a point cloud 48 of location data points 46 that are, in turn, acquired in the manner described above (Step 102). In an exemplary embodiment, the processing apparatus 16 is configured to form the point cloud 48. In another exemplary embodiment, the processing apparatus 16 is configured to obtain the point cloud 48 from a memory or some other component that is electrically connected to and configured for communication with the processing apparatus 16. In either instance, the processing apparatus 16 is configured to process the location data points 46 of the point cloud 48 to generate or construct the geometry surface model of the cardiac structure (Step 104). Any number of techniques known in the art may be used to process the location data points 46 for this purpose. One exemplary technique involves the use of an alpha shape algorithm to construct the geometry surface model. An example of such a technique is described in U.S. Patent Publication No. 2009/0167755 filed on Dec. 28, 2007, and entitled "Method and System for Generating Surface Models of Geometric Structures," the entire disclosure of which is incorporated herein by reference. It will be appreciated that while the description below is limited to an embodiment wherein an alpha shape technique is used to construct the geometry surface model, the present disclosure is not meant to be so limited. Rather, techniques known in the art other than the alpha shape technique, or alpha shape techniques other than that specifically described herein, may be used, and therefore, remain within the spirit and scope of the present disclosure.

Figure 6:
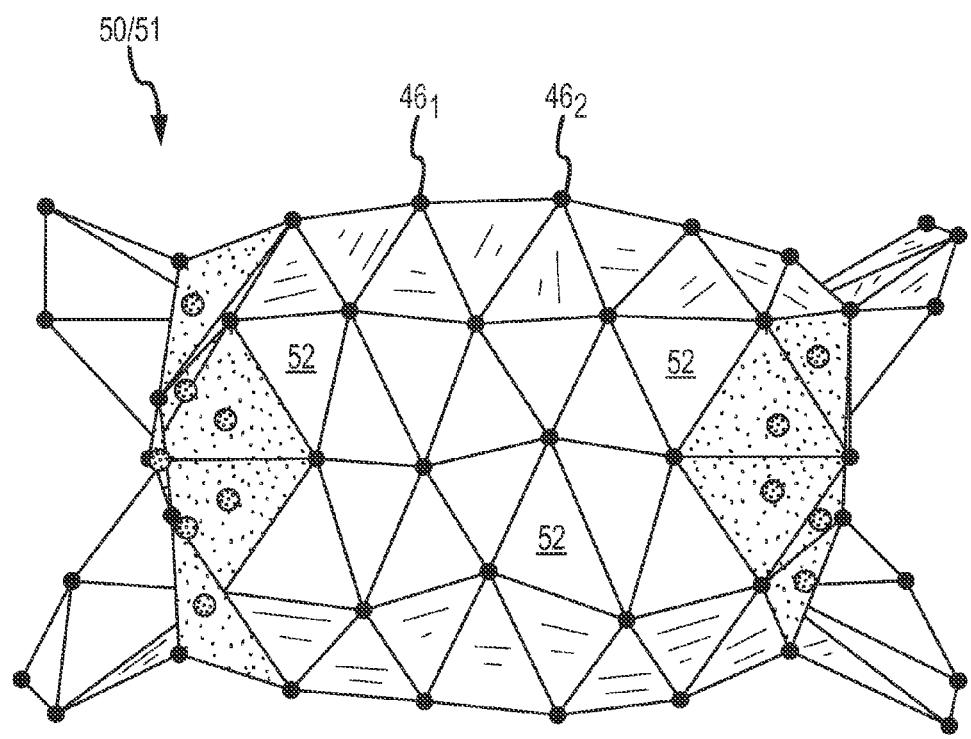
FIG. 6 is a schematic diagram of a computed alpha shell of the point cloud illustrated in FIG. 3.

Thus, with continued reference to FIG. 5, in an exemplary embodiment, the location data points 46 of the point cloud 48 are subjected to an alpha shape algorithm to compute an alpha shell 50, and therefore, a geometric surface model 51, corresponding to the cardiac structure. FIG. 6 is illustrative of the alpha shell 50 of the point cloud 48 depicted in FIG. 3. To compute or generate the alpha shell 50, the processing apparatus 16 triangulates the location data points 46 in the point cloud 48 to form one or more facets 52 that, when take together, create or form the alpha shell 50, and therefore, a geometry surface model, corresponding to the cardiac structure. Accordingly, as illustrated in FIG. 6, the alpha shell 50 created by this process results in a geometry surface model 51 having a multi-faceted surface wherein each location data point 46 comprises a vertex of the geometry surface model 51, and each facet 52 comprises a triangle, and therefore, has three edges 54. Once the alpha shell 50 has been computed, it may be displayed on a display, such as, for example, the display 44, and/or saved to a memory or storage device associated with, or electrically connected to and configured for communication with, the processing apparatus 16, such as, for example, the memory 47.

As those of ordinary skill in the art will appreciate, the more facets an alpha shell has, the more detail of the underlying structure is represented. The number of facets, and therefore, the level of detail, is dependent on the particular value of alpha ("α") (a measure of distance on the order of millimeters) that is used in the algorithm. For example, if α=0, the alpha shell is simply the original set of location data points 46 comprising the point cloud 48. On the other hand, if α=∞, the alpha shell is simply the convex hull of the point cloud 48. Thus, if the α value is relatively small, the alpha shell will have a greater degree of detail (i.e., more facets) and may allow for concave portions of the cardiac structure to be modeled.

Accordingly, a value of α between zero and infinity (i.e., 0<α<∞) is chosen or otherwise determined, and is used by the processing apparatus 16 to generate an alpha shell, and therefore, geometry surface model, having a corresponding degree of detail. Typically, the α value will be on the order of five (5) to ten (10) millimeters, however, the present disclosure is not meant to be so limited. Rather, in alternate embodiments, α values that are more or less than those values specifically identified herein may be used, and as such, remain within the spirit and scope of the present disclosure. In an exemplary embodiment, the α value may be set as part of the set-up of the system 10, and the processing apparatus 16, in particular (i.e., during manufacture of the system 10 or during the initialization of the system 10 and prior to use). Further, the value may be non-adjustable or it may be adjustable by the user of the system 10 using, for example, a user interface 53 (best shown in FIG. 1), such as, for example, a touch screen, a keyboard, a keypad, a slider control, a mouse, a graphical user interface having one or more user-selectable or user-inputtable fields, or some other user-controllable input device electrically connected to the processing apparatus 16 to allow the user to set or adjust the α value.

In another exemplary embodiment, rather than computing the alpha shell as described above, the alpha shell may be computed or constructed wherein different regions of the computed alpha shell have different levels of detail. In such an embodiment, each of the location data points 46 in the point cloud 48 is assigned a weight. The weight is a factor that determines how much detail the clinician/physician wants to preserve in that particular area or region of the cardiac structure. If a greater amount of detail is desired, the weight is lower; conversely, if a lesser amount of details is desired, the weight is higher. Accordingly, in such an embodiment, once all of the location data points 46 are acquired or collected, each location data point 46 is assigned a weight by the processing apparatus 16 that may be, for example, inversely proportional to the local location data point density surrounding that particular location data point 46, directly proportional to the distance to the closest neighboring location data point 46 in the point cloud 48, or directly proportional to the average distance of a particular number of closest location data points 46 in the point cloud 48. Thus, the overall level of detail of the alpha shell 50 depends on the density of the location data points 46 in each region of the cardiac structure. Accordingly, depending on the weights assigned to the location data points 46, particular portions or regions of the alpha shell 50, and therefore, geometry surface model 51, may have different levels of detail. This concept is commonly referred to as weighted alpha shapes, and thus, in such an embodiment, the alpha shell 50 is computed as a weighted alpha shape.

Irrespective of whether a "regular" or a "weighted" alpha shape-based geometry surface model is constructed, it is generally desirable that each edge 54 of each facet 52 be shared by no more than one other neighboring or adjacent facet 52 (i.e., each edge 54 of the alpha shell 50 is shared by no more than two adjacent facets 52). However, due to the level of detail the alpha shape algorithm may provide, it is possible that one or more edges 54 of a particular facet 52 in the completed/generated alpha shell 50 will be shared by more than one other adjacent facet 52. This results in a alpha shell that is considered to be non-manifold, which makes it difficult, if not impossible, to determine what the true outer surface of the alpha shell 50 is, and what surface in the alpha shell 50 is actually inside the outer surface (in other words, it is difficult to tell in which direction the surface in the alpha shell is actually facing). In the event that this occurs, it may be desirable to perform a post-processing procedure to "clean up" the generated alpha shell 50 in order to provide a geometry surface model of the cardiac structure that has a smooth, simplicial surface.

Figure 7:
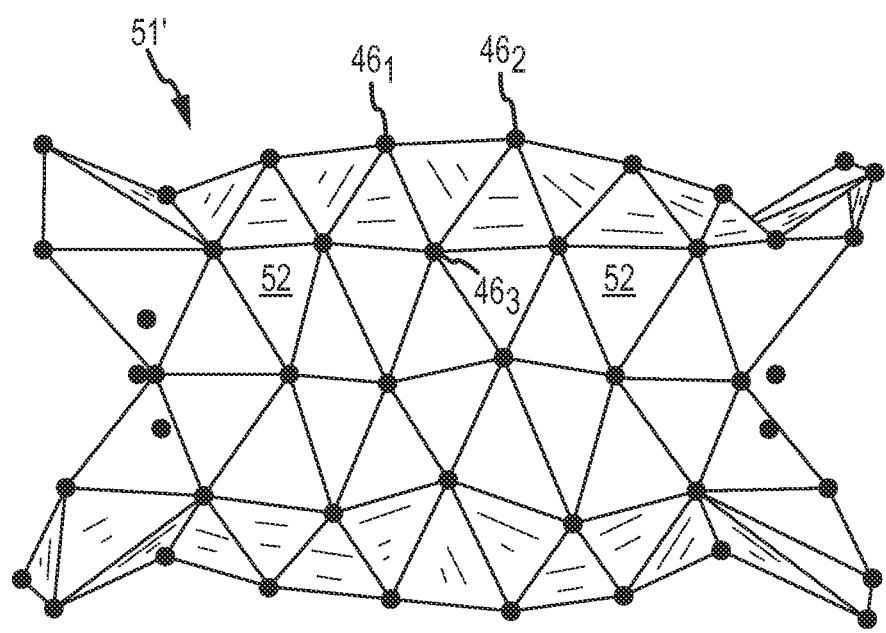
FIG. 7 is a schematic diagram of simplicial surface model generated from the alpha shell illustrated in FIG. 6.

In the context of this application, the term "simplicial surface" is intended to mean "a connected, orientable, and locally a two-dimensional manifold surface" (i.e., each edge 54 in the alpha shell 50 is shared by no more than two adjacent facets 52). In other words, for each facet 52 having at least one edge 54 that is shared by more than one other neighboring/ adjoining facets 52, it must be determined which of the adjacent facets 52 will be kept as part of the final geometry surface model 51 having a smooth, simplicial surface, and which ambiguous adjacent facet(s) 52 will be discarded (See, for example, FIG. 6 wherein several "ambiguous adjacent" facets are identified by stippling and are discarded in the post-processing procedure). This procedure ensures that in the final geometry surface model, each edge 54 of each facet 52 is shared by no more than one other neighboring facet 52. Accordingly, in an exemplary embodiment, the processing apparatus 16 is configured to perform a post-processing procedure on a generated or computed alpha shell to generate a geometry surface model having a smooth, simplicial surface that is based on the computed alpha shell. (Step 106). Thus, as illustrated generally in FIG. 5, and in greater detail in FIG. 8, the processing apparatus 16 may be configured to process the alpha shell 50 with a simplicial surface or "skin" algorithm to generate a geometry surface model 51' that has a smooth, simplicial surface (best shown in FIG. 7).

Figure 8:
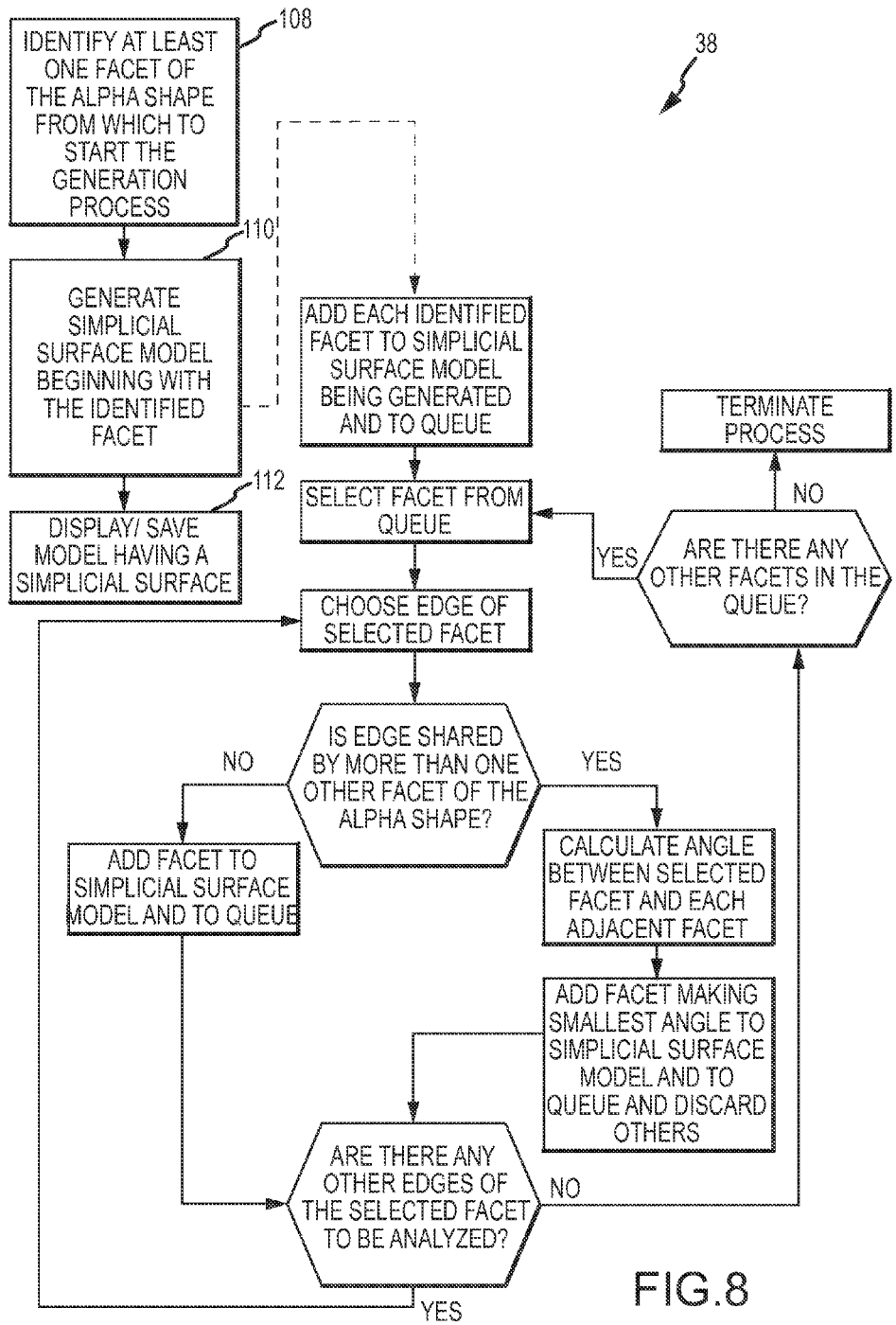
FIG. 8 is a flow chart illustrating an exemplary method of generating a simplicial surface model in accordance with the present teachings.

With reference to FIGS. 5 and 8, an exemplary embodiment of such a post-processing procedure will now be described. In an exemplary embodiment, the processing apparatus 16 is configured to identify at least one location data point 46 (i.e., vertex), facet 52, or edge 54 of the alpha shell 50, and therefore, geometry surface model 51, from which to begin the generation process (Step 108). In an exemplary embodiment, this "start point" is a point 46, facet 52, and/or edge 54 of the alpha shell 50 that is shared by the convex hull of the point cloud 48.

Figure 9:
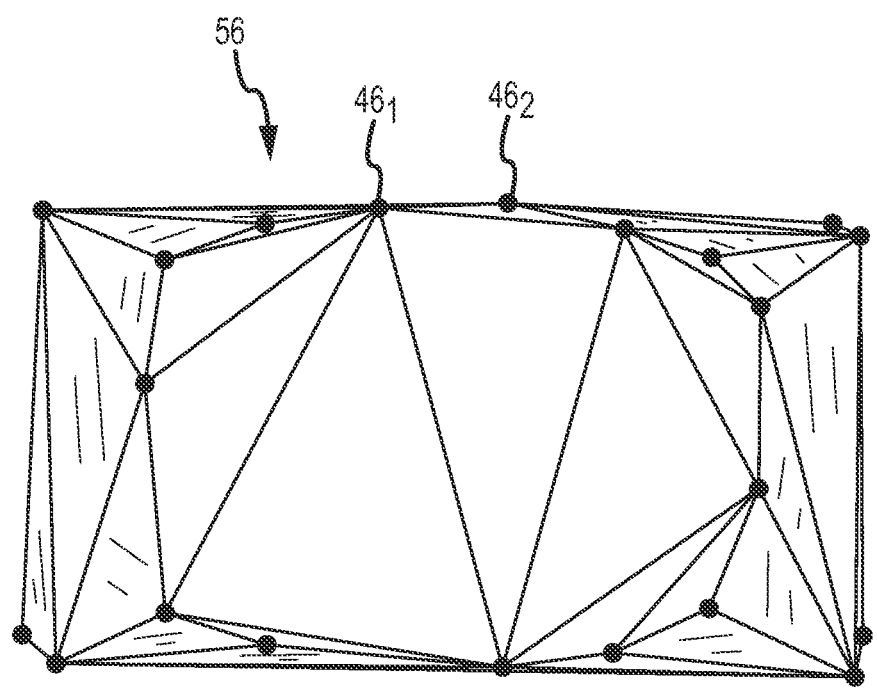
FIG. 9 is a schematic diagram of the convex hull of the point cloud illustrated in FIG. 3.

Accordingly, in one exemplary embodiment, the identification of the start point is accomplished by computing the convex hull of the point cloud 48, and then comparing the convex hull with the alpha shell 50, which also corresponds to the point cloud 48. In such an embodiment, the processing apparatus 16 is configured to compute the convex hull of the point cloud 48 using one of any number of known techniques or convex hull algorithms. The resulting surface model generated by the convex hull algorithm, which is illustrated in FIG. 9 and identified therein as reference numeral 56, represents connections between the most exterior location data points 46 of the point cloud 48, and therefore, a surface model comprising the outermost surfaces of the cardiac structure is generated.

In this particular embodiment, once the convex hull 56 has been computed or generated, the processing apparatus 16 is configured to compare the convex hull 56 with the alpha shell 50. In an exemplary embodiment, the processing apparatus 16 compares the alpha shell 50 and the convex hull 56 to determine whether any facets 52 of the alpha shell 50 are shared by the convex hull 56. In such an embodiment, each facet 52 of the alpha shell 50 that is also part of, or shared by, the convex hull 56 is identified and, for reasons more fully described below, placed into a queue stored in a memory or storage device associated with, or electrically connected to and configured for communication with, the processing apparatus 16, such as, for example, the memory 47. These "shared" facets 52 are identified to provide a starting point for generating the simplicial geometry surface model 51' since these facets 52 are known to be on the outside surface of the cardiac structure because, by definition, anything on the convex hull is necessarily on the outside surface of the structure to which the convex hull corresponds. Thus, by identifying such facets 52, the processing apparatus 16 knows that the identified facets 52 are correctly oriented and on the outermost surface. In addition to being placed in a queue, the identified facets 52 are also added to the final simplicial geometry surface model 51' illustrated in FIG. 7 that is being generated or computed by the processing apparatus 16.

It should be noted, however, that it may not be necessary for the processing apparatus 16 to compute the convex hull 56 separately in order to identify the shared points, edges, or facets. In an alternate exemplary embodiment, whether or not one or more facets 52 of the alpha shell 50 is shared by the convex hull 56 can be determined from the alpha shell 50 itself. More specifically, each facet 52 has two opposite vertices in the underlying triangulation that is performed by the processing apparatus 16 when executing the alpha shape algorithm, which has essentially divided all of three-dimensional space into tetrahedra. Alpha shape facets 52 that are also on the convex hull 56 (i.e., shared by the convex hull 56) will have the "point at infinity" as one of their two opposite vertices. This theoretical point is part of all the exterior tetrahedral of the convex hull 56, and therefore, the processing apparatus 16 executing the simplicial surface algorithm can determine whether a particular facet 52 of the alpha shell 50 is shared by the convex hull 56 by determining whether one of its opposing vertices is the "point at infinity." Accordingly, the present disclosure is not meant to be limited to any one singular way or technique of identifying points, edges, or facets of the alpha shell 50 that are shared by the convex hull 56. Rather, techniques other than those described with specificity herein remain within the spirit and scope of the present disclosure.

Regardless of how shared facets are determined, once one or more facets 52 of the alpha shell 50 is identified as being shared by the convex hull 56 and placed in the queue, the processing apparatus 16 is configured to evaluate or process each of these facets 52 in the queue (and those subsequently added to the queue) one at a time, to generate the final simplicial geometry surface model 51' (Step 110). More particularly, the processing apparatus 16 takes and analyzes a first facet 52 in the queue, and for each edge 54 thereof determines how many neighboring or adjacent facets 52 share that particular edge 54. If an edge 54 of the evaluated facet 52 is not shared by any other facets 52, then, generally speaking, that edge is left as a boundary edge in the simplicial geometry surface model 51'. If an edge 54 of the evaluated facet 52 is shared by only one other adjacent facet 52, then that adjacent facet 52 is added to the simplicial geometry surface model 51' and also added to the queue for future processing/evaluation. If, however, an edge 54 of the evaluated facet 52 is shared by two or more other adjacent facets 52 (e.g., the edge 54 is shared by a total of three or more facets 52), the processing apparatus 16 must choose which adjacent facet 52 to include in the simplicial geometry surface model 51', and which facets 52 to discard.

Figure 10:
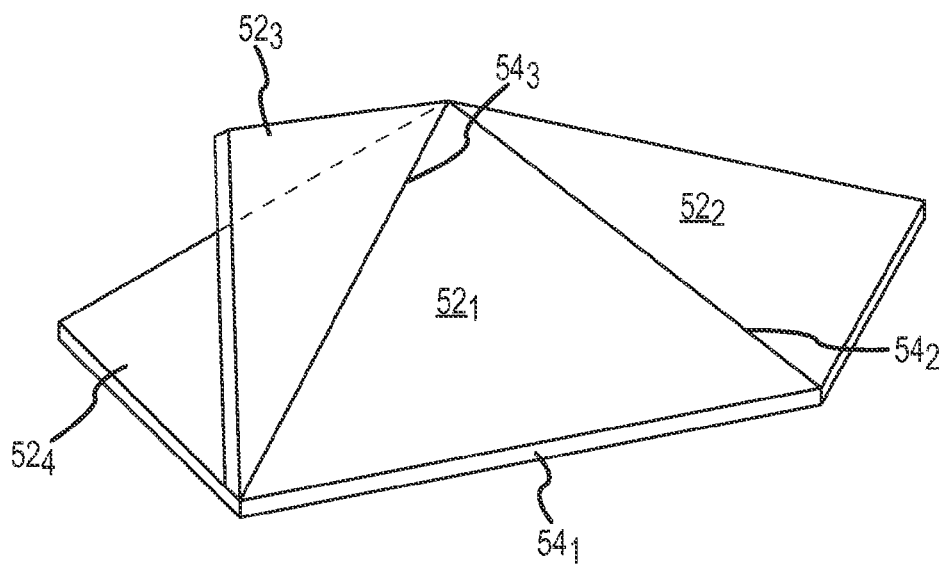
FIG. 10 is a schematic view of a portion of the surface of an alpha shape such as that illustrated in FIG. 6.

For purposes of illustration, FIG. 10 depicts a portion of the surface of an exemplary alpha shell, which does not necessarily correspond to the alpha shell 50 illustrated in FIG. 6. In FIG. 10, the alpha shell has a facet $52_1$ that has been identified as a "shared" facet, and includes edges $54_1$-$54_3$. With respect to edge $54_1$, since no other facets 52 share this edge, edge $54_1$ would be left as a boundary edge of the simplicial geometry surface model 51'. With respect to edge $54_2$, since this edge is shared by only one other adjacent facet 52 (facet $52_2$), this facet $52_2$ would be added to the simplicial geometry surface model 51' and also placed in the queue for future analysis or evaluation. With respect to edge $54_3$, since this edge is shared by two other adjacent facets 52 (facets $52_3$ and $52_4$) in addition to facet $52_1$, the processing apparatus 16 must select one of the facets $52_3$ and $52_4$ to be added to the simplicial geometry surface model, and then discard the remaining facet.

To do so, in an exemplary embodiment, the processing apparatus 16 considers each adjacent facet 52 that shares the given edge 54 with the evaluated facet 52 and chooses the one that is the furthest outside, or in other words, closest to the convex hull 56. In order to determine which facet 52 is the furthest outside, the processing apparatus 16 takes into account the angle between the facet 52 being evaluated/analyzed (i.e., the facet $52_1$, for example) and the other adjacent facets 52 sharing the particular edge 54 (e.g., facets $52_3$ and $52_4$), and chooses the adjacent facet 52 making the smallest angle with the evaluated facet 52 (i.e., the smallest dihedral angle).

Figure 11A:
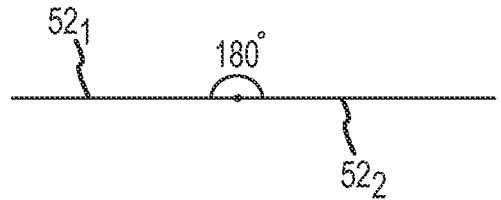
FIGS. 11A-11D are diagrammatic views of various arrangements of adjacent facets of the alpha shape illustrated in FIG. 6.
Figure 11B:
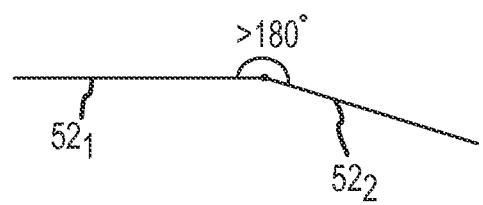
Figure 11C:
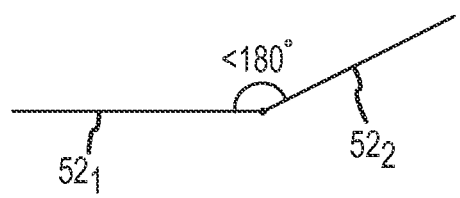
Figure 11D:
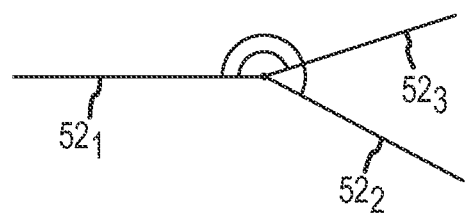

This particular technique may be better understood with reference to FIGS. 11A-11D. With respect to FIG. 11A, adjacent facets $52_1$ and $52_2$ form a flat surface. Accordingly, the dihedral angle between these to facets 52 would be 180 degrees. Alternatively, with respect to FIG. 11B, the adjacent facet $52_2$ is disposed "interior" to facet $52_1$, and therefore, its dihedral angle will be greater than 180 degrees. Conversely, with respect to FIG. 11C, the adjacent facet $52_2$ is disposed "outside" of the facet $52_1$, and therefore, its dihedral angle is less than 180 degrees. In any of the FIGS. 11A-11C, because the facet $52_2$ is the only other facet sharing the particular edge with the facet $52_1$, the facet $52_2$ would be added to the simplicial geometry surface model 51' in each instance. However, FIG. 11D illustrates an instance wherein two facets, facets $52_3$ and $52_4$, share a single edge with the facet $52_1$. Accordingly, in such an instance, only one of facet $52_3$ and facet $52_4$ may be selected to be added to the simplicial geometry surface model 51'. Based on the criterion described above, since the dihedral angle between the facets $52_1$ and $52_3$ is less than that between the facets $52_1$ and $52_4$, the facet $52_3$ would be selected for addition to the simplicial geometry surface model 51', and the facet $52_4$ would be discarded. Accordingly, the facet $52_3$ would be oriented to match the facet $52_1$ (i.e., its vertices are reversed if they do not traverse the vertices of the common edge in the opposite order as the selected facet does), added to the simplicial geometry surface model 51' being generated, and also added to the queue for later analysis.

In an exemplary embodiment, it may be desirable to set a maximum threshold for an acceptable dihedral angle so that the processing apparatus 16 leaves a boundary in the simplicial geometry surface model 51' instead of creating sharp creases and going into cavities of the alpha shell 50. For example, in one embodiment, a maximum threshold angle may be set at 240 degrees. Accordingly, in such an embodiment, if the angle between the evaluated facet 52 and any adjacent facets 52 exceeds (or, in another embodiment, meets or exceeds) the 240 degree threshold, that adjacent facet 52 is not added, or if other facets 52 share the edge 54 but the respective angles between those facets 52 and the evaluated facet 52 are greater than (or, in another embodiment, are equal to or greater than) the threshold value, those adjacent facets 52 are discarded and the particular edge 54 being shared by these two or more facets 52 is left as a boundary edge in the simplicial geometry surface model 51'.

Once each edge 54 of a facet 52 being evaluated has been analyzed as set forth above, the processing apparatus 16 is configured to determine whether there are any other facets 52 in the queue that need to be analyzed. If there are, the processing apparatus 16 takes the next facet 52 in the queue and performs the same analysis described above. Once the last facet 52 in the queue has been analyzed, the processing apparatus 16 is configured to terminate the algorithm, indicating that all allowable neighboring/adjacent facets 52 have been propagated and added to the simplicial geometry surface model 51'.

It should be noted that while the description above relating to the generation of a geometry surface model 51' having a simplicial surface was primarily based on the facets 52 of the alpha shell 50 that are shared by the convex hull 56, the present disclosure is not meant to be so limited. Rather, in certain instances, there may not be any facets 52 of the alpha shell 50 that are shared by the convex hull 56. In such instances, the processing apparatus 16 is configured to evaluate those points 46 (vertices) or edges 54 of the alpha shell 50 that are shared by the convex hull 56 in the manner described in, for example, U.S. Patent Publication No. 2009/0167755 filed on Dec. 28, 2007, and entitled "Method and System for Generating Surface Models of Geometric Structures," the entire disclosure of which was incorporated by reference above.

If, after the above-described process is complete, the generated simplicial geometry surface model 51' includes undesirable voids or holes, these voids or holes may be optionally filled in using various algorithms or techniques known in the art to generate a smoother or more complete model. One exemplary embodiment of such an algorithm that is executable by, for example, the processing apparatus 16, is that described in U.S. Pat. No. 7,825,925 entitled "Method and System for Repairing Triangulated Surface Meshes," the entire disclosure of which is incorporated herein by reference. To summarize, a void or hole in the simplicial geometry surface model 51' is first identified by the processing apparatus 16. The hole is defined by a plurality of hole edges (i.e., boundary edges 54 of facets 52 bordering the hole, for example). Second, the processing apparatus 16 determines a plurality of hole vertices that define the plurality of hole edges. Third, the processing apparatus fills in the hole using one or more triangular facets, not unlike facets 52 described above.

This "filling-in" of the hole may include a series of steps. For example, in a first step, the processing apparatus 16 selects a pair of hole vertices that are not connected by a hole edge. In one embodiment, this step includes selecting the closest pair of hole vertices. Alternatively, this step includes locating the smallest interior angle of the plurality of hole edges, and selecting a pair of hole vertices that define a pair of the plurality of hole edges that intersect at the smallest interior angle of the plurality of hole edges. Once a pair of hole vertices are selected, in a subsequent step, the processing apparatus 16 defines a fabricated edge that connects the selected pair of hole vertices. Next, the processing apparatus 16 determines whether one or more triangles are formed using the defined fabricated edge. If one or more triangles are formed, the processing apparatus 16 defines the newly formed triangles as new facets, and adds them to the simplicial geometry surface model 51'. If, however, one or more triangles are not formed, the processing apparatus 16 continues to define fabricated edges until one or more triangles are formed. This process is then repeated until the identified hole, and any other hole in the simplicial geometry surface model 51', has been filled in to create a void-free simplicial geometry surface model.

It will be appreciated that the "hole filling" technique described above may also be applied in an instance wherein the alpha shell 50 is not subjected to the post-processing procedure described above to generate a simplicial geometry surface model. Therefore, the above described "hole filling" process is also applicable in the instance wherein the geometry surface model 51 includes undesirable holes or voids, and may be performed in the same manner described above with respect to the simplicial geometry surface model 51'.

Additionally, in the event the geometry surface model 51 (or geometry surface model 51') has more than one component, the clinician/physician may be given choices or options as to what to do with the multiple components. These choices or options may include, without limitation, keeping all components as part of the model, keeping only the component having the largest surface area, or trying to connect the components using a stitching algorithm.

In an exemplary embodiment, the processes or methodologies described above may be used to generate a somewhat dynamic geometry surface model of a cardiac structure by generating separate geometry surface models for a plurality of different timepoints in the cardiac cycle of the heart. Accordingly, using the various steps of the process described above, location data points 46 corresponding to the cardiac structure are collected during the different timepoints in the cardiac cycle, thereby creating point clouds 48 for each timepoint in the cardiac cycle. Using the methodologies described above, geometry surface models 51 can be generated for each point cloud 48 and then the respective geometry surface models can be used together or separately for various purposes.

In any event, once a complete or final geometry surface model 51, which hereinafter is meant to encompass both geometry surface model 51 and simplicial geometry surface model 51' described above, is generated, the processing apparatus 16 may be configured to display the geometry surface model 51 on, for example, the display 44 (Step 112). In addition, or alternatively, the processing apparatus 16 may be configured to save the geometry surface model 51' to a memory or storage device associated with, or electrically connected to and configured for communication with, the processing apparatus 16, such as, for example, the memory 47, for later use and/or for the purposes to described below (Step 112).

As was described above, in addition to being configured to obtain (e.g., construct or generate, or otherwise acquire) a geometry surface model of the cardiac structure, the processing apparatus 16 is further configured to construct an EP map corresponding to the cardiac structure. Accordingly, upon the completion of, or simultaneous with, the construction of the geometry surface model 51 corresponding to at least a portion of the cardiac structure, the processing apparatus 16 is further configured to map EP information onto the geometry surface model 51, and thus, to construct an EP map of the cardiac structure. The EP information that is mapped onto the geometry surface model 51 may relate to one or more EP parameters of the cardiac structure, such as, for example and without limitation, those described in great detail in U.S. Pat. No. 7,774,051 entitled "System and Method for Mapping Electrophysiology Information onto Complex Geometry," the entire disclosure of which is incorporated herein by reference. To summarize, however, the EP parameters may include, for example, voltage measurements, peak-to-peak voltage measurements, electrograms, complex fractionated electrograms (CFE), and other time- and frequency-domain EP information. For purposes of illustration and clarity, the description below will be limited to an embodiment wherein a single EP parameter of interest is measured and mapped onto the geometry surface model 51. It will be appreciated by those of ordinary skill in the art, however, that in other exemplary embodiments, multiple EP parameters may be measured, and in certain embodiments, mapped onto the surface model either alone or in combination with each other. Accordingly, embodiments wherein more than one EP parameter is measured, or measured and mapped onto the surface model, remain within the spirit and scope of the present disclosure.

Figure 12A:
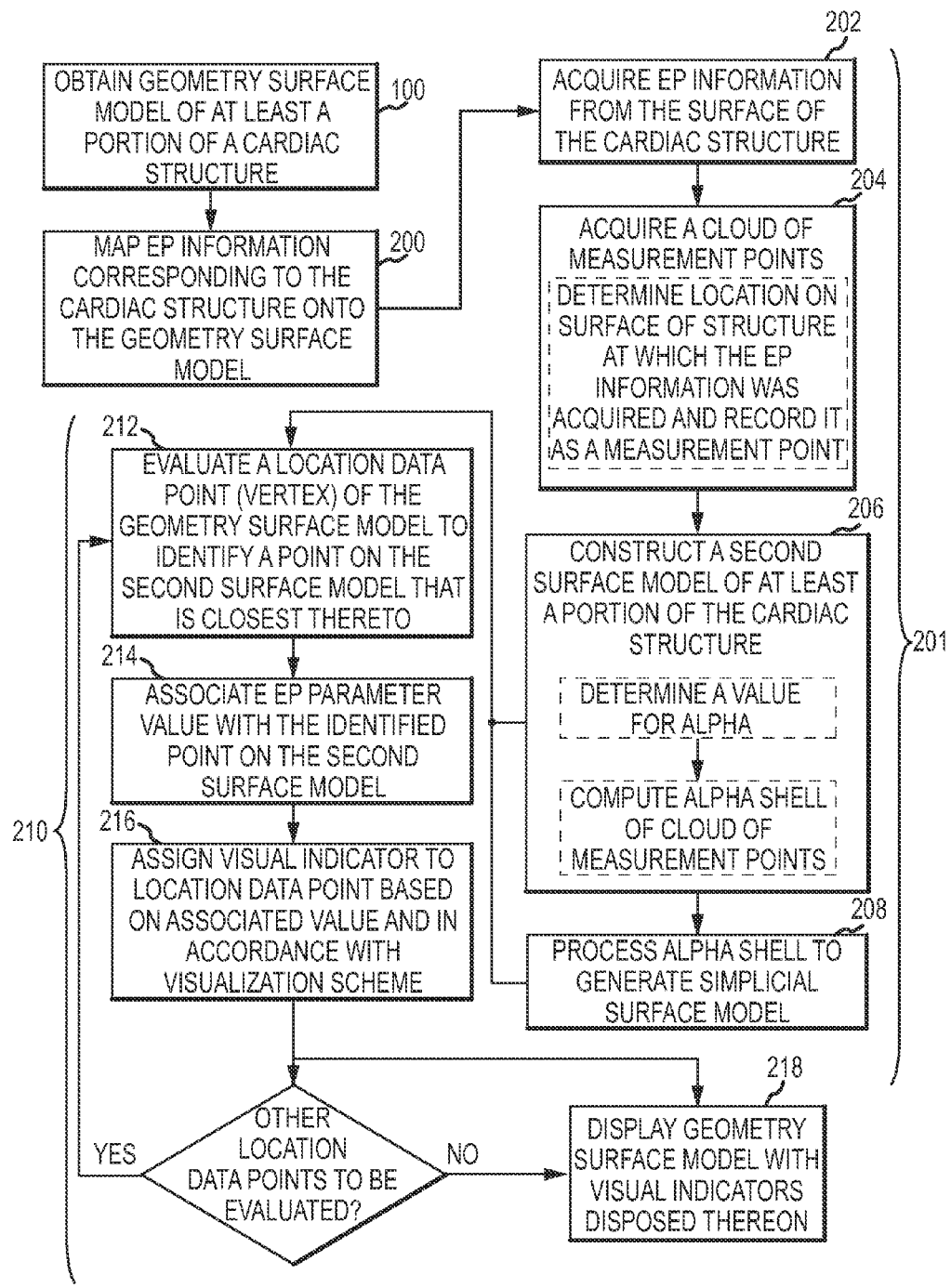
FIG. 12A is a flow chart illustrated an exemplary method of mapping electrophysiological information onto a multi-dimensional geometry surface model of an anatomic structure in accordance with the present teachings.

With reference to FIG. 12A, to construct the EP map the processing apparatus 16 is configured to first acquire EP information to be mapped onto the surface model 51 (Step 202). More particularly, as the sensor 32 (or sensors 32, in an embodiment wherein multiple sensors are used) is moved along the surface of the cardiac structure, the sensor 32 is configured to make one or more measurements of an EP parameter of interest. In an exemplary embodiment, a measurement of the EP parameter is made in response to a user command. More particularly, in an exemplary embodiment, the system 10 further comprises the user input device 53 (best shown in FIG. 1), which may comprise a touch screen, a keyboard, a keypad, a button, a mouse, a graphical user interface having one or more user-selectable or user-inputtable fields, or some other user-controllable input device that is electrically connected to the processing apparatus 16, through which a user may issue a command to make an EP parameter measurement. Alternatively, the processing apparatus 16 may be configured to automatically make such a measurement upon detecting that an event, such as, for example, an activation, has occurred, or otherwise determines or detects that the information relating to the EP parameter being measured is reliable. In any event, by virtue of the sensor 32 being electrically connected to the processing apparatus 16, once a measurement is made or taken, an electrical signal produced by the sensor 32 and representative of the measured value of the EP parameter is communicated to the processing apparatus 16.

Figure 13:
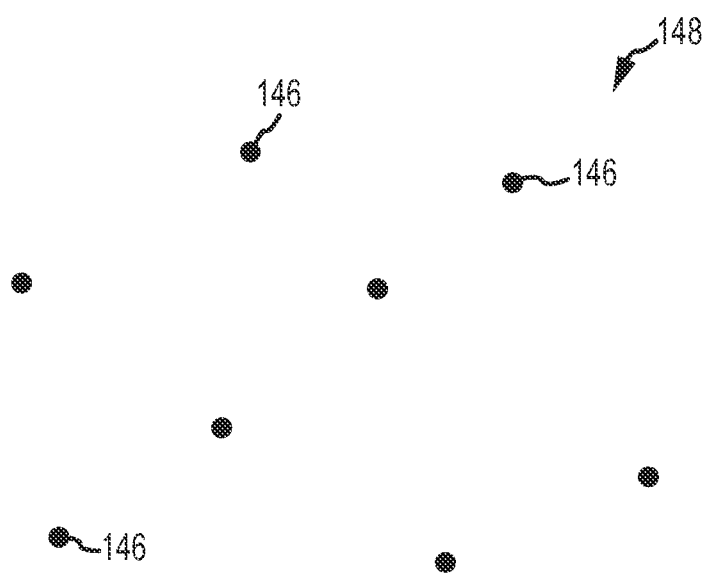
FIG. 13 is a schematic diagram of point cloud comprised of a collection of measurement points corresponding to respective locations on the surface of an anatomic structure at which measurements of an electrophysiological parameter were made.

Regardless of how a measurement is triggered, each time a measurement is made, the processing apparatus 16 is configured to determine the location (position and orientation) of the sensor 32 that made the measurement. The location is recorded as a measurement point 146 corresponding to the location on the surface of the cardiac structure at which the measurement was made or taken in a memory or storage device associated with, or accessible by, the processing apparatus 16, such as, for example, the memory 47. Each measurement point 146 is also associated and recorded with the measured EP parameter value that corresponds to that particular measurement point 146. In an exemplary embodiment, the processing apparatus 16 is configured to determine the location of the sensor 32, and therefore, the corresponding measurement point 146, in the same manner as that described above with respect to the determination of the location of the sensor 32 and the corresponding location data point 46. As such, the description set forth above applies here with equal weight and will not be repeated, rather it is incorporated here by reference. The collection of measurement points 146 taken over time results in the formation of a point cloud 148 (best shown in FIG. 13) stored in a memory or storage device (such as the memory 47), which, along with the EP information represented by the EP parameter values corresponding to each measurement point 146, may be used by the processing apparatus 16 to construct the EP map.

More particularly, once one or more EP parameter values are acquired, the processing apparatus 16 is configured to construct another surface model of the cardiac structure (or at least a portion thereof) using the measurement points 146. This surface model is different than, and in addition to, the surface model 51 described above. To avoid confusion, the surface model 51 will be described below as the "first" surface model (or first surface model 51), while the surface model constructed from the measurement points 146 will be described below as the "second" surface model (or second surface model 151). The second surface model may be constructed in the same manner as that described above with respect to the generation or construction of the first surface model 51 with the exception that the measurement points 146 are used rather than the location data points 46. Accordingly, with that lone exception, the description set forth above relating to the generation or construction of the first surface model 51 applies here with equal weight and will not be repeated in its entirety, rather it is incorporated here by reference.

To summarize, however, and with continued reference to FIG. 12A, the processing apparatus 16 is configured to first acquire a point cloud 148 of measurement points 146 that are, in turn, acquired as described above (Step 204). In an exemplary embodiment, the processing apparatus 16 is configured to form the point cloud 148. In another exemplary embodiment, the processing apparatus 16 is configured to obtain the point cloud 148 from a memory or some other component that is electrically connected to and configured for communication with the processing apparatus 16. In either instance, the processing apparatus 16 is configured to process the measurement points 146 of the point cloud 148 to generate or construct the second surface model 151 of the cardiac structure (Step 206). Any number of techniques known in the art may be used to process the measurement points 146 for this purpose. One exemplary technique involves the use of an alpha shape algorithm to construct the second surface model. An example of such a technique is described in U.S. Patent Publication No. 2009/0167755 filed on Dec. 28, 2007, and entitled "Method and System for Generating Surface Models of Geometric Structures," the entire disclosure of which was is incorporated by reference above. It will be appreciated that while the description below is limited to an embodiment wherein an alpha shape technique is used to construct the second surface model, the present disclosure is not meant to be so limited. Rather, techniques known in the art other than the alpha shape technique, or alpha shape techniques other than that specifically described herein may be used, and therefore, remain within the spirit and scope of the present disclosure.

Figure 14:
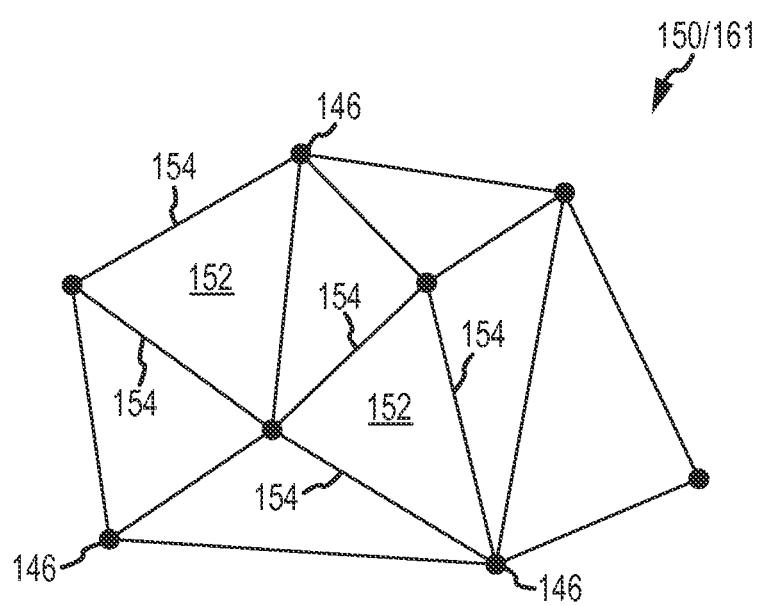
FIG. 14 is a schematic diagram of a computed alpha shell of the point cloud illustrated in FIG. 13.

Thus, with continued reference to FIG. 12A, in an exemplary embodiment, the measurement points 146 of the point cloud 148 are subjected to an alpha shape algorithm to compute an alpha shell 150, and therefore, a surface model 151, corresponding to the cardiac structure (or at least a portion thereof). FIG. 14 is illustrative of a portion of the alpha shell 150 of the point cloud 148 depicted in FIG. 13. To compute or generate the alpha shell 150, the processing apparatus 16 triangulates the measurement points 146 in the point cloud 148 to form one or more facets 152 that, when taken together, create or form the alpha shell 150, and therefore, a surface model, corresponding to the cardiac structure. Accordingly, as illustrated in FIG. 14, the alpha shell 150 created by this process results in the surface model 151 (i.e., the second surface model 151) having a multi-faceted surface wherein each measurement point 146 comprises a vertex of the surface model 151 and each facet 152 comprises a triangle, and therefore, has three edges 154. Once the alpha shell 150 has been computed, it may be saved to a memory or storage device associated with, or electrically connected to and configured for communication with, the processing apparatus 16, such as, for example, the memory 47, and used as will be described below.

As those of ordinary skill in the art will appreciate, the more facets an alpha shell has, the more detail of the underlying structure is represented. The number of facets, and therefore, the level of detail, is dependent on the particular value of alpha ("α") (a measure of distance on the order of millimeters) that is used in the algorithm. For example, if α=0, the alpha shell is simply the original set of measurement points 146 comprising the point cloud 148. On the other hand, if α=∞, the alpha shell is simply the convex hull of the point cloud 148. Thus, if the α value is relatively small, the alpha shell will have a greater degree of detail (i.e., more facets) and may allow for concave portions of the cardiac structure to be modeled.

Accordingly, a value of α between zero and infinity (i.e., 0<α<∞) is chosen or otherwise determined, and is used by the processing apparatus 16 to generate the alpha shell 150, and therefore, the second surface model 151, having a corresponding degree of detail. Typically, the α value will be on the order of five (5) to ten (10) millimeters, however, the present disclosure is not meant to be so limited. Rather, in alternate embodiments, α values that are more or less than those values specifically identified herein may be used, and as such, remain within the spirit and scope of the present disclosure. In an exemplary embodiment, the α value may be set as part of the set-up of the system 10, and the processing apparatus 16, in particular (i.e., during manufacture of the system 10 or during the initialization of the system 10 and prior to use). Further, the value may be non-adjustable or it may be adjustable by the user of the system 10 using, for example, the user interface 53 (best shown in FIG. 1). In an exemplary embodiment, the same α value is used to construct the first and second surface models 51, 151. In other exemplary embodiments, however, different α values are used. For example, in one exemplary embodiment, the α value used to construct the second surface model 151 is greater than that used to construct the first surface model 51.

In an exemplary embodiment, a post-processing technique may be performed on the alpha shell 150 to generate a simplicial surface model 151' (Step 208). In such an embodiment, simplicial surface model 151' may be generated in the same manner described above and as illustrated in FIGS. 5 and 8 with respect to the generation of the simplicial surface model 51'. Accordingly, the description set forth above relating to the generation of the simplicial surface model 51' applies here with equal weight and will not repeated, rather, the description set forth above is incorporated here by reference.

In another exemplary embodiment, rather than the processing apparatus 16 constructing or generating the second surface model 151 as described above, the processing apparatus 16 is configured to acquire the second surface model 151 from a memory or another component that is associated with or accessible by the processing apparatus 16. Accordingly, the processing apparatus 16 may obtain the second surface model 151 in a number of ways, each of which remains within the spirit and scope of the present disclosure.

Once the processing apparatus 16 obtains (e.g., constructs or generates, or otherwise acquires) the second surface model 151, which hereinafter is meant to encompass both surface models 151 and 151' described above, the processing apparatus 16 is configured to evaluate, as will be described below, one or more of the location data points 46 (i.e., vertices) of the first surface model 51. Based on that evaluation, the processing apparatus is further configured to assign visual indicators to one or more of those location data points 46 based on one or more of the measured EP parameter values, and in accordance with a visualization scheme corresponding to the EP parameter being measured (Step 210). In an exemplary embodiment, every location data point 46 of the first surface model 51 is evaluated in the manner described below. Alternatively, in another exemplary embodiment wherein one or more regions of the cardiac structure are of interest (rather than the entire structure), only those location data points 46 disposed in an area or areas of the first surface model 51 corresponding to the region or regions of interest are evaluated in the manner described below (as opposed to all of the location data points 46 of the first surface model 51 being evaluated). In either instance, in an exemplary embodiment, each location data point 46 that is to be considered or evaluated is placed into a queue stored in, for example, a memory or other storage device associated with, or accessible by, the processing apparatus 16, such as, for example, the memory 47. The processing apparatus 16 then evaluates in turn each location data point 46 in the queue in the manner described below.

Accordingly, for each location data point 46 that is to be evaluated, the processing apparatus 16 is configured, in an exemplary embodiment, to identify a point on the second surface model 151 that is closest in distance to that location data point 46 (Step 212). More particularly, the processing apparatus 16 is configured to process the first and second surface models 51, 151 to determine and identify the point on the second surface model 151 that is closest to the evaluated location data point 46 of the first surface model 51. The identified point on the second surface model 151 may comprise a point on an edge 154 of a facet 152, a point disposed within a facet 152, or a measurement point 146 (i.e., vertex of the second surface model 151). In an exemplary embodiment, the processing apparatus 16 is configured to identify the closest point by computing the distance between the location data point 46 and the edges 154, facets 152, and measurement points 146 or vertices of the second surface model 151, and then determining a point that is the closest to the location data point 46.

Once the point on the second surface model 151 is identified, the processing apparatus 16 is configured to associate an EP parameter value with the identified point (Step 214). In an exemplary embodiment, the EP parameter value may be associated with the identified point using known interpolation techniques or schemes, such as, for example, those described in U.S. Pat. No. 7,774,051, the entire disclosure of which was incorporated herein by reference above. For instance, in one exemplary interpolation scheme, if the identified point is determined to be within the interior of one of the facets 152, the EP parameter value associated with the identified point will be interpolated using the barycentric interpolation technique based on the EP parameter values measured at each of the measurement points 146 that comprise the vertices that define the facet 152. If, however, the identified point either lies on or is very close to an edge 154 of the second surface model 151, the EP parameter value associated with the identified point will be bi-linearly interpolated from the respective EP parameter values measured at the two measurement points 146 that define the subject edge 154. Finally, if the identified point is determined to be close enough to a measurement point 146 (i.e., closer to a measurement point 146 than to any other edge 154 or facet 152 of the second surface model 151), the EP parameter value measured at that measurement point 146 is correlated with the identified point.

Figure 12B:
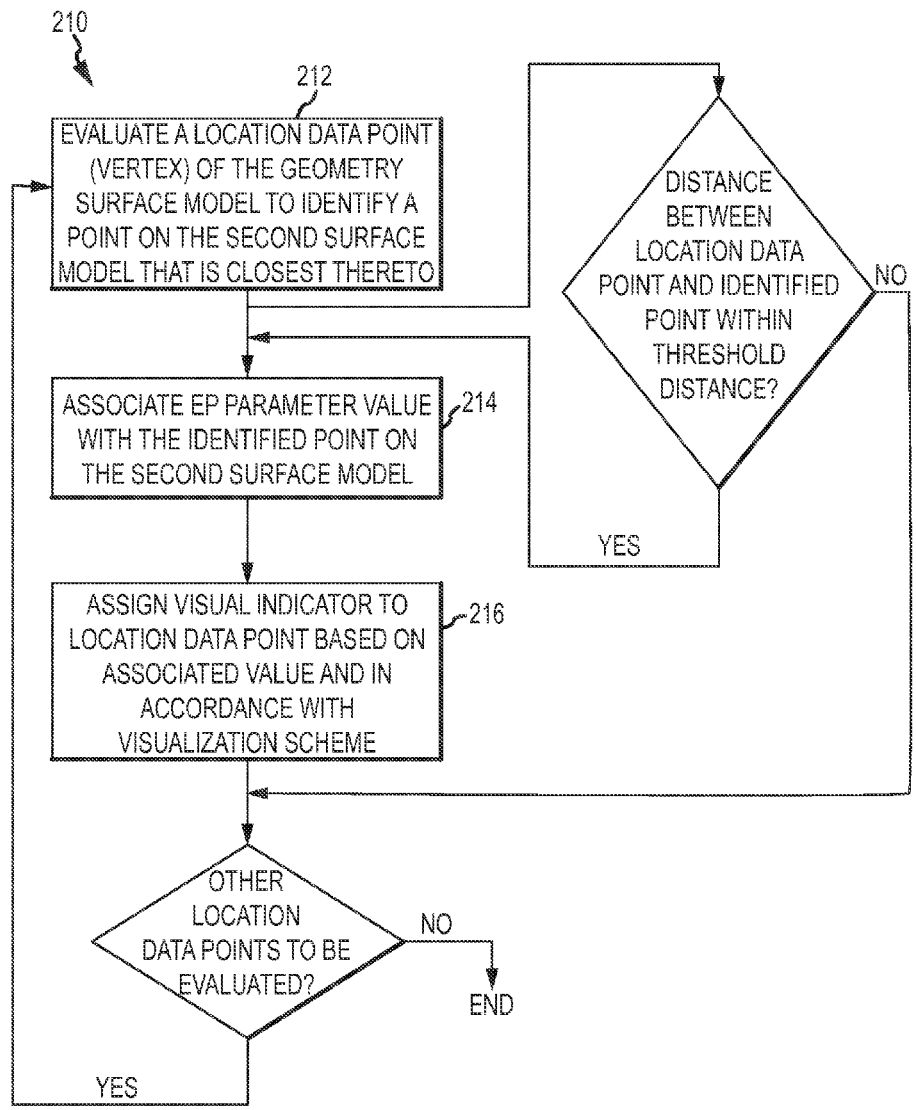
FIG. 12B is flow chart illustrating an exemplary embodiment of the evaluating and visual indicator assignment step of the method illustrated in FIG. 12A.

In another exemplary embodiment, and as illustrated in FIG. 12B, the processing apparatus 16 is configured to evaluate the distance between the location data point 46 and the corresponding identified point on the second surface model 151 prior to associating a EP parameter value therewith and/or, as will be described below, assigning a visual indicator to the location data point 46. More particularly, the processing apparatus 16 may be programmed with a predetermined threshold distance and may be configured to compare the distance between the location data point 46 and the identified point with the threshold distance (Step 214). In an exemplary embodiment, if the distance exceeds (or, in another embodiment, meets or exceeds) the threshold distance, no EP parameter value is associated with the identified point, and either no visual indicator or a default visual indicator is assigned to the location data point using the visual indicator assignment process described below. The process is then repeated for the next location data point 46 to be evaluated or considered (i.e., the next location data point in the queue). If there are no more location data points 46 to be evaluated or considered, the visual indicator assignment process is ended. Alternatively, if the distance falls below (or, in another embodiment, meets or falls below) the threshold distance, the process continues as described below.

In an exemplary embodiment, the threshold distance is a multiple of the α value used to construct the first geometry surface model 51. For example, in one embodiment, the threshold distance is equal to the α value, while in another exemplary embodiment, the threshold distance is 2α. In any event, the threshold distance may be set as part of the set-up of the system 10, and the processing apparatus 16, in particular (i.e., during manufacture of the system 10 or during the initialization of the system 10 and prior to use). Further, the value may be non-adjustable or it may be adjustable by the user of the system 10 using, for example, the user interface 53 (best shown in FIG. 1).

Once an EP parameter value is associated with the identified point on the second surface model 151, the processing apparatus 16 is configured to assign a visual indicator to the location data point 46 based on the EP parameter value associated with the identified point and in accordance with a predetermined visualization scheme corresponding to the particular EP parameter (Step 216). More particularly, in an exemplary embodiment, the processing apparatus 16 is configured to first associate one of a number of visualization schemes with the particular EP parameter being mapped. Exemplary visualization schemes include, for example and without limitation, color coding schemes, volumizing schemes, texturizing schemes, and translucency schemes.

Each of the visualization schemes includes a plurality of visual indicators that are used to represent different values of the associated EP parameter. For example, if a color coding visualization scheme is associated with the EP parameter, one color may be assigned to a first value or range of values of the EP parameter, a second color may be assigned to a second value or range of values, and so on and so forth. Similarly, different shades of the same color or different grayscales may be assigned to different values or ranges of values of the EP parameter. Accordingly, each visualization scheme comprises a plurality of visual indicators, wherein each indicator corresponds to a certain value or range of values of the EP parameter with which the visualization scheme is associated. Thus, the processing apparatus 16 is programmed such that each visual indicator is associated with a particular value or range of values for the EP parameter associated therewith. Further, because in an exemplary embodiment the same visualization scheme may be used for different EP parameters at different times, the processing apparatus 16 is configured and programmed such that for each EP parameter with which a visualization scheme may be associated, the visual indicators thereof are in turn associated with corresponding values or ranges of values for that particular EP parameter. Accordingly, the processing apparatus 16 may be configured to allow each visualization scheme to be used for multiple EP parameters. The processing apparatus 16 may be pre-programmed with the respective EP parameter/visualization scheme associations, or the processing apparatus 16 may make the association in response to user inputs received from, for example, the user input device 53.

Once a visualization scheme is associated with the EP parameter, the processing apparatus 16 is configured to evaluate the EP parameter value associated with the identified point on the second surface model 151 and to assign the location data point 46 a visual indicator of the visualization scheme corresponding to the associated EP parameter value. More particularly, the processing apparatus 16 is configured to look up the EP parameter value in a look-up table, for example, to determine which of the visual indicators of the visualization scheme corresponds to the EP parameter value. The processing apparatus 16 is then configured to assign the visual indicator to the location data point 46. Accordingly, in an embodiment wherein the visualization scheme is a color coding scheme, the color red may be assigned to the location data point 46. This process is then repeated for the next location data point 46 of the first surface model 51 that is to be evaluated or considered (i.e., the next location data point in the queue). If there are no other location data points 46 in the queue, the process is ended.

Figure 15:
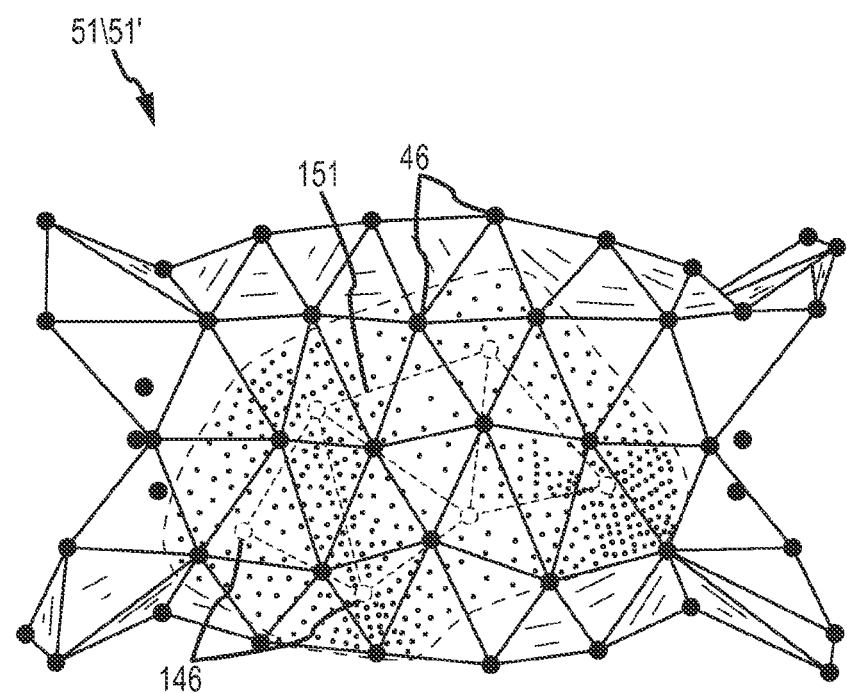
FIG. 15 is a schematic diagram of a geometry surface model corresponding to the point cloud illustrated in FIG. 3 depicting electrophysiological information being mapped thereon.

As illustrated in FIG. 12A, once visual indicators have been assigned to one or more location data points 46 of the first surface model 51 (or each time a visual indicator is assigned to a location data point 46), the processing apparatus 16 is configured to employ known computer graphics techniques to render an EP map on the surface model 51, as is well known in the art, and to then control the display device 44 of the system 10 to display the surface model 51 with the EP information corresponding to the EP parameter mapped thereon (Step 218). FIG. 15 illustrates an example of the surface model 51 having an exemplary or representative EP map rendered thereon. It should be noted that FIG. 15 further includes a depiction of an exemplary surface model 151 and corresponding measurement points 146 that are used to generate the EP map. It will be appreciated that the surface model 151 and measurement points 146 depicted in FIG. 15 do not necessarily correspond to those illustrated in FIGS. 13 and 14, but rather are provided simply to illustrate an example of the rendering of an EP map onto the surface model 51.

It will be appreciated that in an exemplary embodiment, the above-described process may be performed to construct an EP map before the geometry surface model (first surface model) of the entire cardiac structure (or a particular desired portion thereof) has been completed (i.e., prior to the surface model 51 representing the entire cardiac structure or desired portion thereof). Rather, so long as the second surface model 151 has been constructed for a region of the cardiac structure corresponding to the first surface model 51, EP information corresponding to that region of the cardiac structure can be mapped onto the first surface model 51, thereby allowing for the real-time and simultaneous construction of the first surface model 51 of the cardiac structure and an EP map corresponding thereto. Thus, as each location data point 46 and/or measurement point 146 is/are added to the respective first and second surface models 51, 151, the above-described process can be repeated to continuously construct the first surface model 51 of the cardiac structure and/or the EP map corresponding thereto, without having to recompute the first surface model 51 and/or the EP map for the entire cardiac structure. Similarly, as each location data point 46 and/or measurement point 146 is/are added to the respective first and second surface models 51, 151, the above-described process can be repeated to update the area(s) or portion(s) of the EP map and/or first surface model 51 that correspond to the regions of the cardiac structure from which the new location data point(s) 46 or measurement point(s) 146 is/are acquired, also without having to recompute the first surface model 51 and/or the EP map for the entire cardiac structure.

It will be appreciated that in addition to the structure of the system 10 described above, another aspect of the present disclosure is a computer-implemented method for constructing an EP map corresponding to an anatomic structure, such as, for example, a cardiac structure. In an exemplary embodiment, and as described above, the model construction system 14 of the system 10, and the processing apparatus 16 thereof, in particular, is configured to perform the methodology. However, as was briefly described above, in other exemplary embodiments, the processing apparatus 16 is configured to perform some, but not all, of the methodology. For example, in an exemplary embodiment, the processing apparatus 16 is not configured to construct or generate one or both of the first and second surface models 51, 151, but rather is configured to obtain the surface model(s) from another component. In such an embodiment, another component or components that is/are part of the system 10 or the model construction system 14 thereof, or that is/are configured for communication with the system 10, and the processing apparatus 16 thereof, in particular, is/are configured to perform some of the methodology.

With reference to FIG. 12A, in an exemplary embodiment the method, in its most general form, includes a step 100 of obtaining a geometry surface model (a first geometry surface model) of a cardiac structure (or at least a portion thereof), and a step 200 of mapping EP information corresponding to the cardiac structure onto the geometry surface model. In an exemplary embodiment, the geometry surface model comprises an alpha shell of a point cloud comprised of a plurality of location data points corresponding to respective locations on the surface of the cardiac structure.

In an exemplary embodiment, and with reference to FIGS. 5 and 12A, the obtaining step 100 comprises acquiring the geometry surface model from a memory or storage device, or some other component. In another exemplary embodiment, the obtaining step 100 comprises constructing the geometry surface model. More particularly, in such an embodiment, the obtaining step 100 comprises a substep 102 of acquiring a cloud of location data points and/or the individual location data points thereof, and another substep 104 of computing an alpha shell of the cloud of location data points. In an exemplary embodiment, the obtaining step 100 further comprises a substep 106 of processing the alpha shell computed in the substep 104 to generate a simplicial surface model.

With continued reference to FIG. 12A, the mapping step 200 may comprise a number of substeps. In an exemplary embodiment, the mapping step 200 comprises a substep 201 of obtaining a surface model (second surface model) of the cardiac structure (or at least a portion thereof). Similar to the geometry surface model described above with respect to step 100, in an exemplary embodiment, the second surface model comprises an alpha shell of a point cloud comprised of a plurality of measurement points corresponding to respective locations on the surface of the cardiac structure at which measurements of an EP parameter were made. The obtaining substep 201 may comprises acquiring the surface model from a memory or storage device, or some other component, or may comprise constructing the surface model.

More particularly, in an embodiment wherein the surface model is constructed, the obtaining substep 201 comprises a step 202 of acquiring EP information from the surface of the cardiac structure, a step 204 of acquiring a cloud of measurement points, and/or the individual measurement points thereof, by determining the locations on the surface of the cardiac structure at which the EP information was acquired, and a step 206 of computing an alpha shell of the cloud of measurement points. In an exemplary embodiment, the substep 201 further comprises a step 208 of processing the alpha shell computed in the step 206 to generate a simplicial surface model.

The mapping step 200 may further comprise a sub step 210 of evaluating one or more of the location data points of the first surface model, and assigning a visual indicator to one or more of the evaluated location data points. In an exemplary embodiment, the substep 210 comprises a step 212 of evaluating a location data point to identify a point on the second surface model that is the closest thereto. More particularly, the evaluating step 212 may comprise processing the first and second surface models to identify the point on the second surface model that is the closest to the evaluated location data point. As described above, the identified point may comprise a point on a facet or edge of the second surface model, or may comprise a measurement point (vertex) of the second surface model.

Once a point on the second surface model has been identified for the evaluated location data point, the substep 210 may further comprise the step 214 of associating a value of the EP parameter being measured with the identified point. The associating step 214 may comprise determining the EP parameter value to be associated with the identified point by (i) interpolating the EP value from a plurality of EP parameter measurements, or (ii) correlating a value of the EP parameter measured at one of the measurement points with the identified point.

In any event, once an EP parameter value is associated with the identified point on the second surface model, the substep 210 comprises a step 216 of assigning a visual indicator to the evaluated location data point based on the EP parameter value associated with the identified point, and in accordance with a visualization scheme corresponding to the EP parameter. In one exemplary embodiment, the visualization scheme corresponding to the EP parameter is a color coding visualization scheme, and the assigning step 216 comprises assigning a visual indicator in the form of a color to the evaluated location data point.

In an exemplary embodiment, the evaluating step 212 described above may further comprise a substep of calculating the distance between the evaluated location data point and the identified point on the second surface model. The evaluating step 212 may further comprise comparing the calculated distance with a predetermined threshold distance. In such an embodiment, the assigning step 216 may comprise assigning a visual indicator to the evaluated location data point only if the calculated distance falls below (or, in another exemplary embodiment, meets or falls below) the threshold distance. Alternatively, a default visual indicator may be assigned to the evaluated location data point when the calculated distance exceeds (or, in another exemplary embodiment, meets or falls below) the threshold distance.

In an exemplary embodiment, once one or more visual indicators have been assigned to one or more corresponding location data points, the mapping step 200 comprises a step 218 of displaying the first surface model with the assigned visual indicators disposed thereon.

It will be appreciated that additional functionality described in greater detail above with respect to the system 10, and the model construction system 14 and processing apparatus 16, thereof, in particular, may also be part of the inventive methodology. Therefore, to the extent such functionality has not been expressly described with respect to the methodology, the description thereof above is incorporated here by reference.

It should be understood that the model construction system 14, and particularly the processing apparatus 16, as described above may include a conventional processing apparatus known in the art, capable of executing pre-programmed instructions stored in an associated memory, all performing in accordance with the functionality described herein. It is contemplated that the methods described herein, including without limitation the method steps of embodiments of the invention, will be programmed in a preferred embodiment, with the resulting software being stored in an associated memory and where so described, may also constitute the means for performing such methods. Implementation of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although only certain embodiments have been described above with a certain degree of particularity, those skilled in the art could make numerous alterations to the disclosed embodiments without departing from the scope of this disclosure. Joinder references (e.g., attached, coupled, connected, and the like) are to be construed broadly and may include intermediate members between a connection of elements and relative movement between elements. As such, joinder references do not necessarily infer that two elements are directly connected/coupled and in fixed relation to each other. Additionally, the terms electrically connected and in communication are meant to be construed broadly to encompass both wired and wireless connections and communications. It is intended that all matter contained in the above description or shown in the accompanying drawings shall be interpreted as illustrative only and not limiting. Changes in detail or structure may be made without departing from the invention as defined in the appended claims.

What is claimed is:

1. A computer-implemented method of constructing an electrophysiological (EP) map corresponding to an anatomic structure, the method comprising:
   obtaining a first surface model of at least a portion of said anatomic structure, said first surface model comprising an alpha shell generated according to an alpha shape algorithm applied to a point cloud comprised of a plurality of location data points corresponding to respective locations on the surface of said anatomic structure;
   obtaining a second surface model of at least a portion of said anatomic structure, said second surface model comprising an alpha shell generated according to an alpha shape algorithm applied to a point cloud comprised of a plurality of measurement points corresponding to respective locations on the surface of said anatomic structure at which measurements of an EP parameter were made;
   processing said first and second surface models to identify, for at least one of said location data points, a point on said second surface model that is closest in distance to said location data point, wherein said identified point has a value of said EP parameter associated therewith; and assigning a visual indicator to said location data point based on said EP parameter value associated with said identified point on said second surface model and in accordance with a visualization scheme corresponding to said EP parameter.

2. The method of claim 1 further comprising the step of associating said EP parameter value with said identified point on said second surface model, said associating step comprising one of:

interpolating said EP parameter value from a plurality of EP parameter measurements; and correlating a value corresponding to an EP parameter measurement made at one of said measurement points with said identified point on said second surface model.

3. The method of claim 1, wherein said visualization scheme is a color-coding scheme, and said assigning step comprises assigning a visual indicator in the form of a color to said location data point.

4. The method of claim 1, wherein said obtaining a first surface model step comprises the step of constructing said first surface model, said constructing step including:

acquiring said plurality of location data points forming said point cloud; and applying an alpha shape to said point cloud to compute said alpha shell.

5. The method of claim 4, wherein said constructing step comprises processing said alpha shell to generate a simplicial surface model.

6. The method of claim 1, wherein said obtaining a second surface model step comprises:

acquiring said plurality of measurement points forming said point cloud; and applying an alpha shape algorithm to said point cloud to compute said alpha shell.

7. The method of claim 6, wherein said constructing step comprises processing said alpha shell to generate a simplicial surface model.

8. The method of claim 1 further comprising the step of calculating the distance between said location data point and said identified point on said second surface model, said assigning step comprising assigning said visual indicator to said location data point if said calculated distance is within a predetermined threshold distance.

9. The method of claim 1 further comprising the step of displaying said first surface model with said visual indicator disposed thereon.

10. A computer-implemented method of constructing an electrophysiological (EP) map corresponding to an anatomic structure, the method comprising:

acquiring a plurality of location data points corresponding to respective locations on the surface of said anatomic structure, said plurality of location data points forming a first point cloud;

generating a first surface model of at least a portion of said anatomic structure by applying an alpha shape algorithm to said first point cloud to compute an alpha shell;

acquiring a plurality of measurement points corresponding to respective locations on the surface of said anatomic structure at which measurements of an EP parameter were made, said plurality of measurement points forming a second point cloud;

generating a second surface model of at least a portion of said anatomic structure by applying an alpha shape algorithm to said second point cloud to compute an alpha shell;

processing said first and second surface models to identify, for at least one of said location data points, a point on said second surface model that is closest in distance to said location data point, wherein said identified point has a value of said EP parameter associated therewith; and assigning a visual indicator to said location data point based on said EP parameter value associated with said identified point on said second surface model and in accordance with a visualization scheme corresponding to said EP parameter.

11. The method of claim 10 further comprising the step of displaying said first surface model with said visual indicator disposed thereon.

12. The method of claim 10, wherein said step of generating said first surface model comprises applying an alpha shape algorithm to said first point cloud using a first alpha value, and said step of generating said second surface model comprises applying an alpha shape algorithm to said second point cloud using a second alpha value that is different than said first alpha value.

13. The method of claim 10 further comprising the step of associating said EP parameter value with said identified point on said second surface model, said associating step comprising one of:

interpolating said EP parameter value from a plurality of EP parameter measurements; and correlating a value corresponding to an EP parameter measurement made at one of said measurement points with said identified point on said second surface model.

14. The method of claim 10, wherein said assigning step comprises assigning a color to said location data point.

15. The method of claim 10, wherein said steps of generating said first and second surface models are performed simultaneously.

16. A system for constructing an electrophysiological (EP) map, comprising:

a processing apparatus comprising a processor, said processing apparatus configured to:

obtain a first surface model of at least a portion of said anatomic structure, said first surface model comprising an alpha shell generated according to an alpha shape algorithm applied to a point cloud comprised of a plurality of location data points corresponding to respective locations on the surface of said anatomic structure;

obtain a second surface model of at least a portion of said anatomic structure, said second surface model comprising an alpha shell generated according to an alpha shape algorithm applied to a point cloud comprised of a plurality of measurement points corresponding to respective locations on the surface of said anatomic structure at which measurements of an EP parameter were made;

identify, for at least one of said location data points, a point on said second surface model that is closest in distance to said location data point, wherein said identified point has a value of said EP parameter associated therewith; and assign a visual indicator to said location data point based on said EP parameter value associated with said identified point on said second surface model and in accordance with a visualization scheme corresponding to said EP parameter.

17. The system of claim 16, wherein said processing apparatus is further configured to associate said EP parameter value with said identified point on said second surface model by one of:

interpolating said EP parameter value from a plurality of EP parameter measurements; and correlating a value corresponding to an EP parameter measurement made at one of said measurement points with said identified point on said second surface model.

18. The system of claim 16, wherein said processing apparatus is configured to obtain said first surface model by:

acquiring said plurality of location data points forming said point cloud; and applying an alpha shape algorithm to said point cloud to compute said alpha shell.

19. The system of claim 16, wherein said processing apparatus is configured to obtain said second surface model by:

acquiring said plurality of measurement points forming said point cloud; and applying an alpha shape algorithm to said point cloud to compute said alpha shell.

20. The system of claim 16 further comprising a display device, said processing apparatus configured to control said display device to display said first surface model with said visual indicator disposed thereon.

* * * * *